(12) United States Patent
Gidwani et al.

(10) Patent No.: US 9,012,464 B2
(45) Date of Patent: Apr. 21, 2015

(54) SALTS AND POLYMORPHIC FORMS OF AFATINIB

(75) Inventors: Ramesh Matioram Gidwani, Maharashtra (IN); Channaveerayya Hiremath, Maharashtra (IN); Manoj Dalsingar Yadav, Maharashtra (IN); Wolfgang Albrecht, Ulm (DE); Dirk Fischer, Frankfurt am Main (DE)

(73) Assignee: Ratiopharm GmbH, Ulm (DE)

( * ) Notice: Subject to any disclaimer, the term of this patent is extended or adjusted under 35 U.S.C. 154(b) by 50 days.

(21) Appl. No.: 13/989,603

(22) PCT Filed: Nov. 23, 2011

(86) PCT No.: PCT/US2011/062031
§ 371 (c)(1),
(2), (4) Date: Sep. 11, 2013

(87) PCT Pub. No.: WO2012/121764
PCT Pub. Date: Sep. 13, 2012

(65) Prior Publication Data
US 2014/0051713 A1    Feb. 20, 2014

(30) Foreign Application Priority Data

Nov. 25, 2010 (IN) .......................... 2807/DEL/2010

(51) Int. Cl.
*C07D 405/12* (2006.01)

(52) U.S. Cl.
CPC ..................................... *C07D 405/12* (2013.01)

(58) Field of Classification Search
CPC .................................................... C07D 405/12
USPC ..................................... 544/293; 514/266.24
See application file for complete search history.

(56) References Cited

U.S. PATENT DOCUMENTS 8,426,586 B2    4/2013    Soyka et al.

FOREIGN PATENT DOCUMENTS

| WO | WO 96/30347 | 10/1996 |
|----|----|----|
| WO | WO 01/94341 | 12/2001 |
| WO | WO 02/50043 | 6/2002 |
| WO | WO 2008/037824 A2 | 4/2005 |
| WO | WO 2010/130758 | 11/2010 |
| WO | WO 2011/003853 A2 | 1/2011 |
| WO | WO 2012121764 A1 * | 9/2012 |

OTHER PUBLICATIONS

Stahl et al., eds., Handbook of pharmaceutical salts. Properties, selection and use (Wiley-VCH, 2008), pp. 265-327.*
International Search Report dated Jul. 5, 2012 issued in related PCT Application No. PCT/US2011/062031.
Anderson, Preparation of Water-Soluble Compounds Through Salt Formation, The Practice of Medicinal Chemistry, 1996.
Brittain, X-Ray Diffraction III: Pharmaceuticals Applications, vol. 16, No. 7, pp. 14-18 (2001).

* cited by examiner

*Primary Examiner* — Kahsay Habte
(74) *Attorney, Agent, or Firm* — Baker & Hostetler LLP

(57) ABSTRACT

Afatinib salts and crystalline forms thereof are described in the present application and processes for their preparation. Crystalline forms of Afatinib are also described in the present application and processes for their preparation. The present invention also includes pharmaceutical compositions of such Afatinib salts and crystalline forms thereof or crystalline forms of Afatinib, methods of their preparation and the use thereof in the treatment of a patient in need thereof.

9 Claims, 10 Drawing Sheets

Figure 1: XRPD of afatinib free base form A
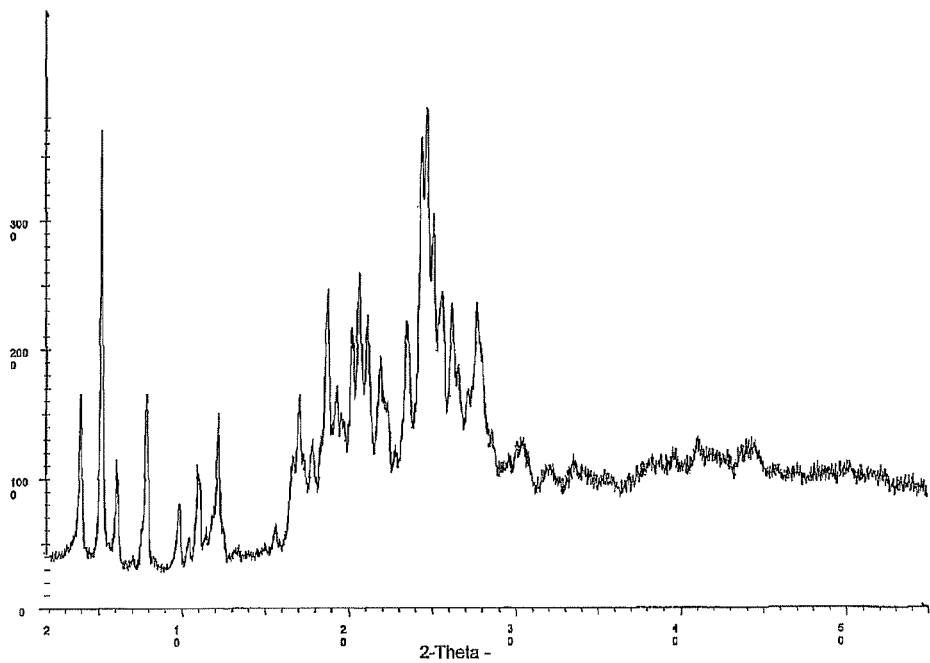
Figure 2: XRPD of afatinib free base form B
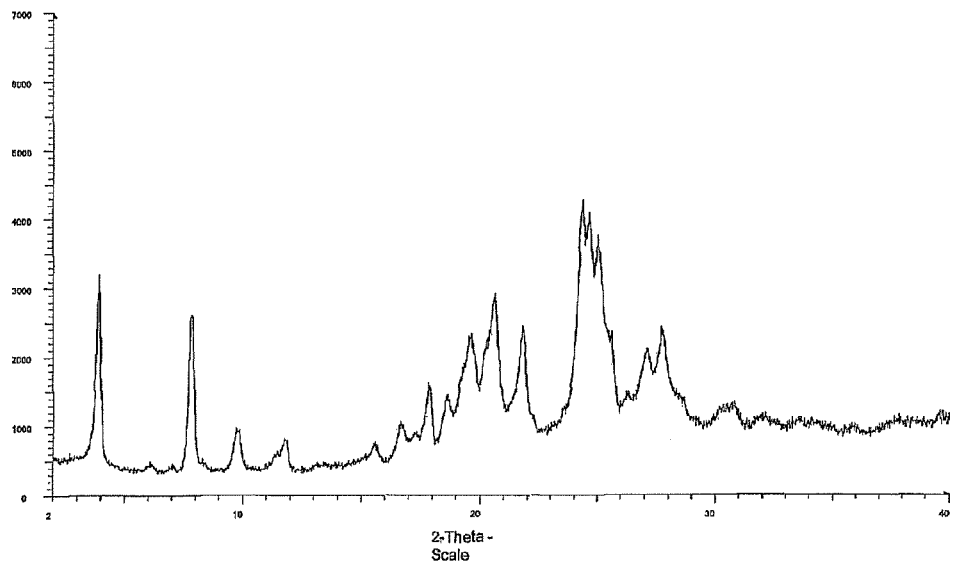

Figure 3: XRPD of afatinib free base form C
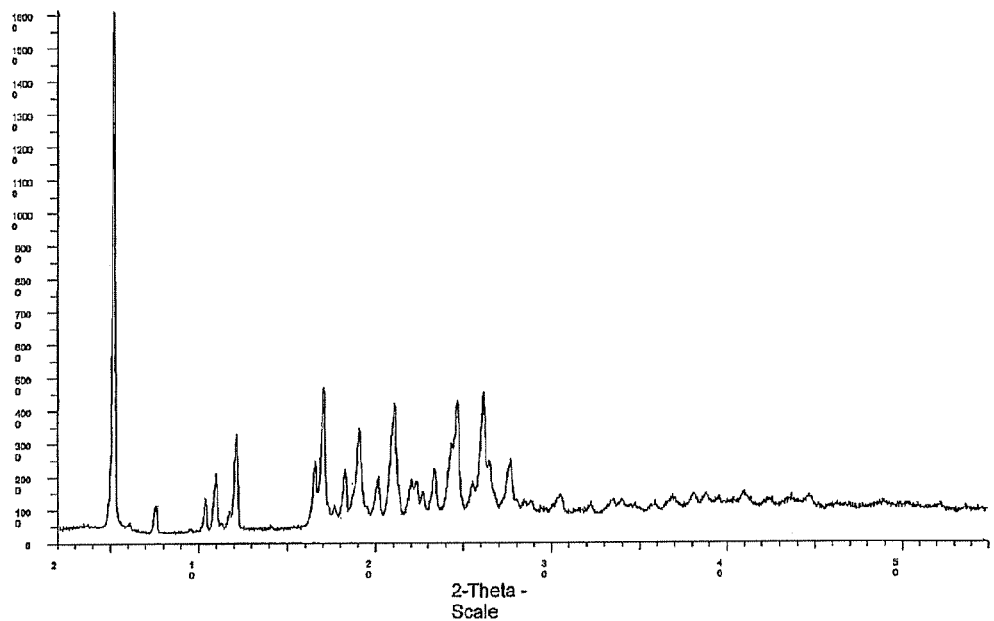
Figure 4: XRPD of afatinib free base form D
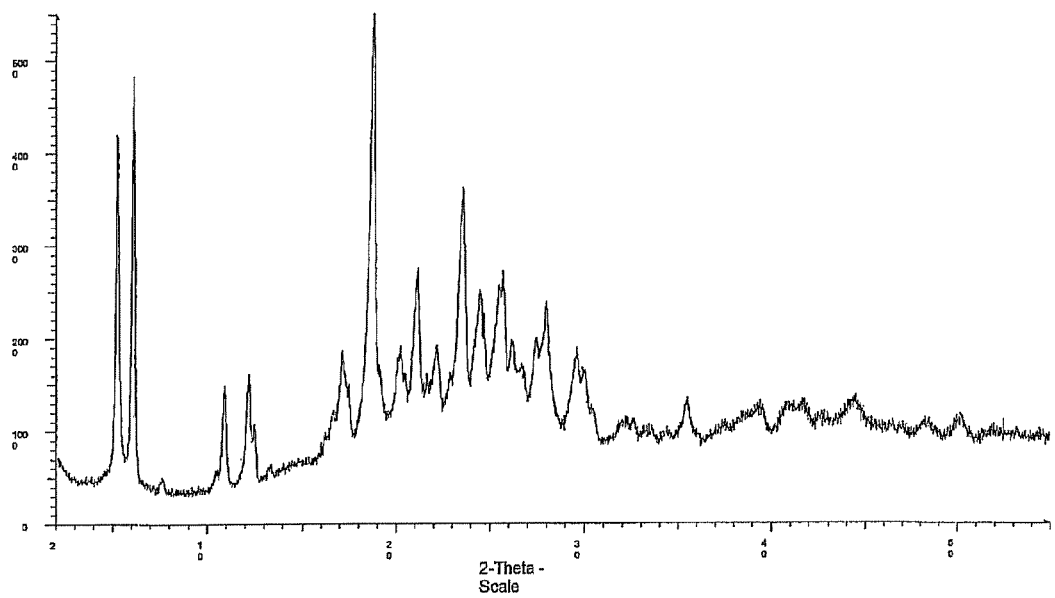

Figure 5: XRPD of afatinib dimaleate salt form B
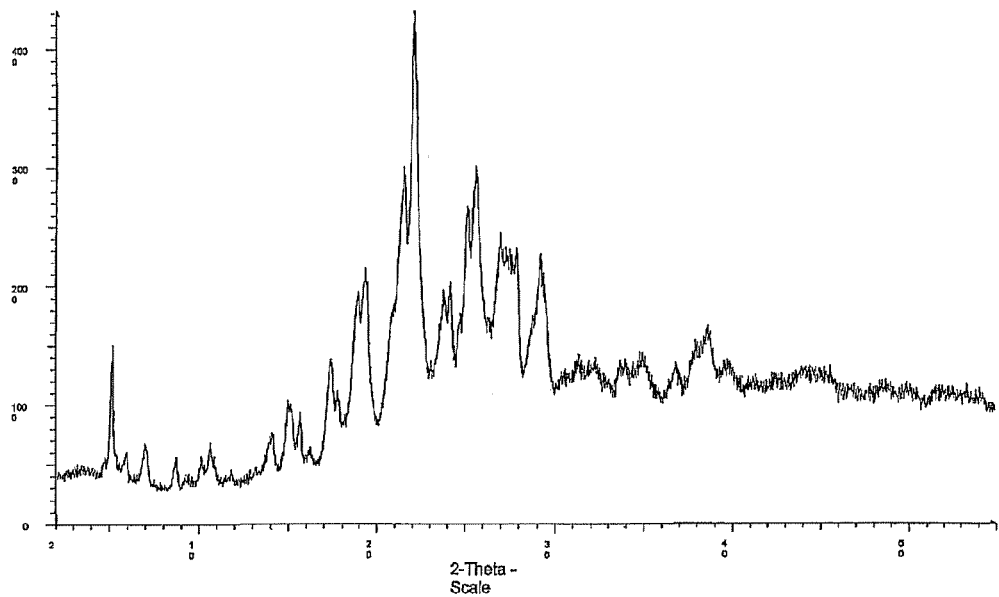
Figure 6: XRPD of afatinib dibenzenesulphonate amorphous
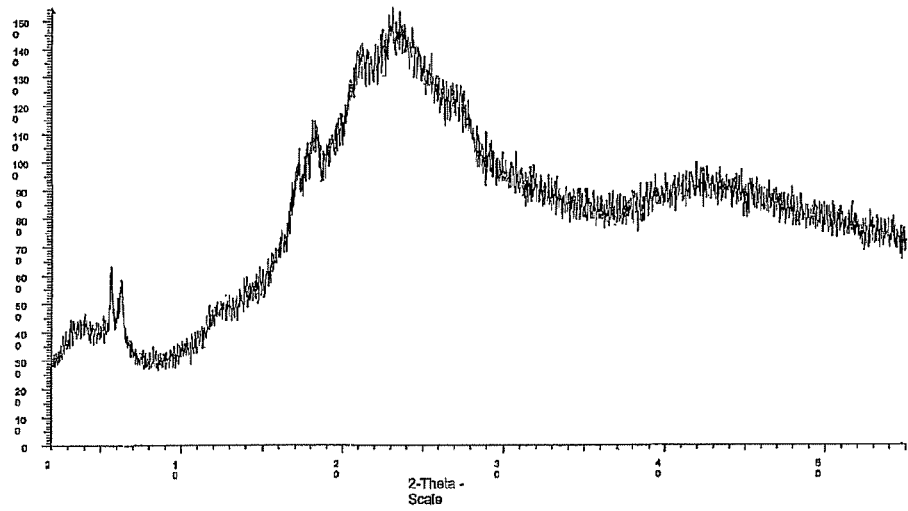

Figure 7: XRPD of afatinib fumarate salt form A
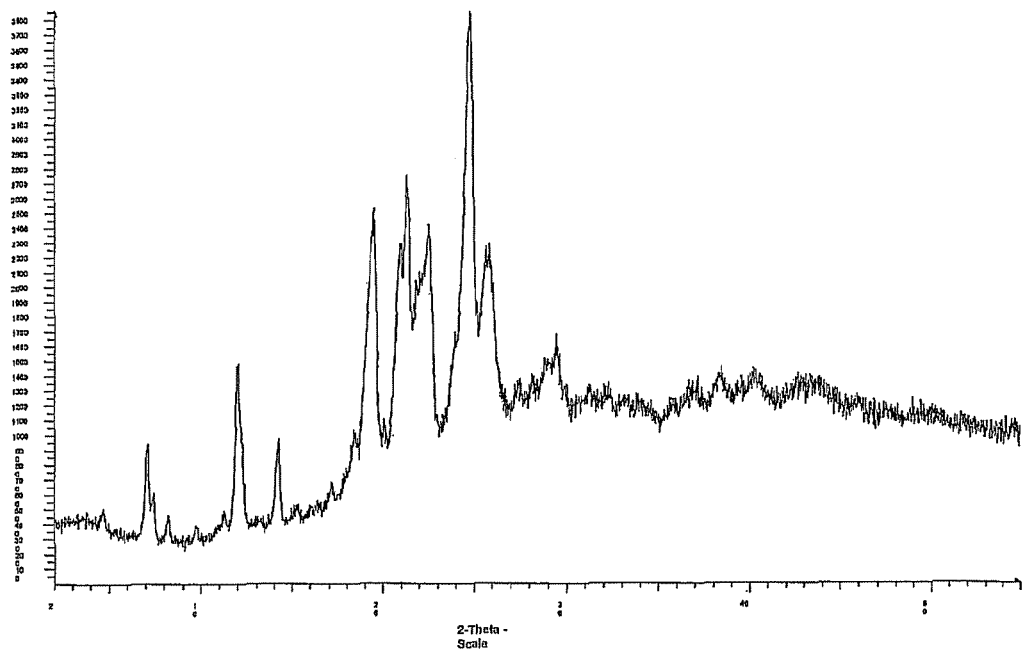
Figure 8: XRPD of afatinib disulphate salt form A
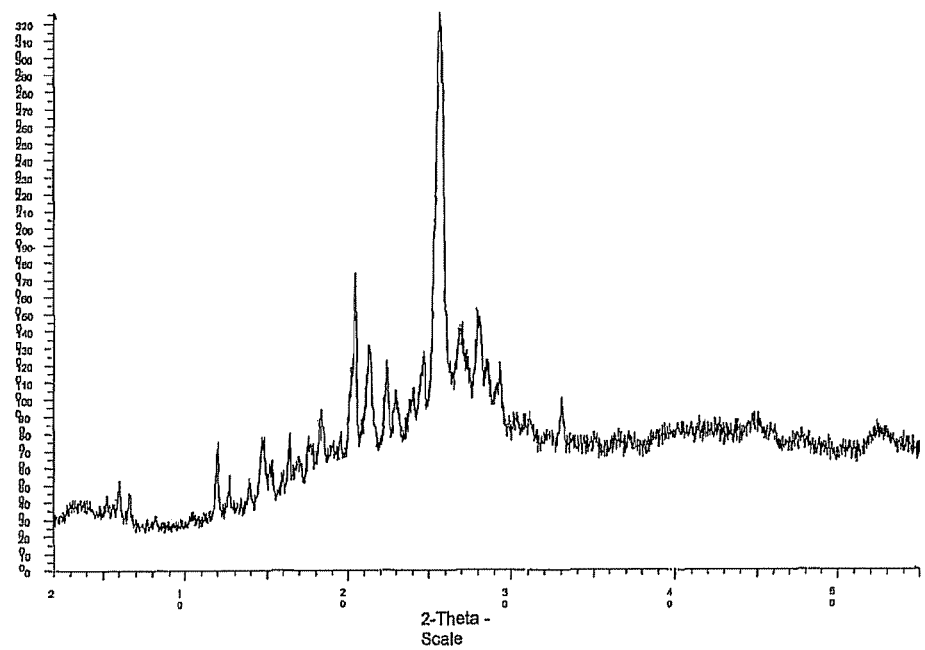

Figure 9: XRPD of afatinib disulphate form B
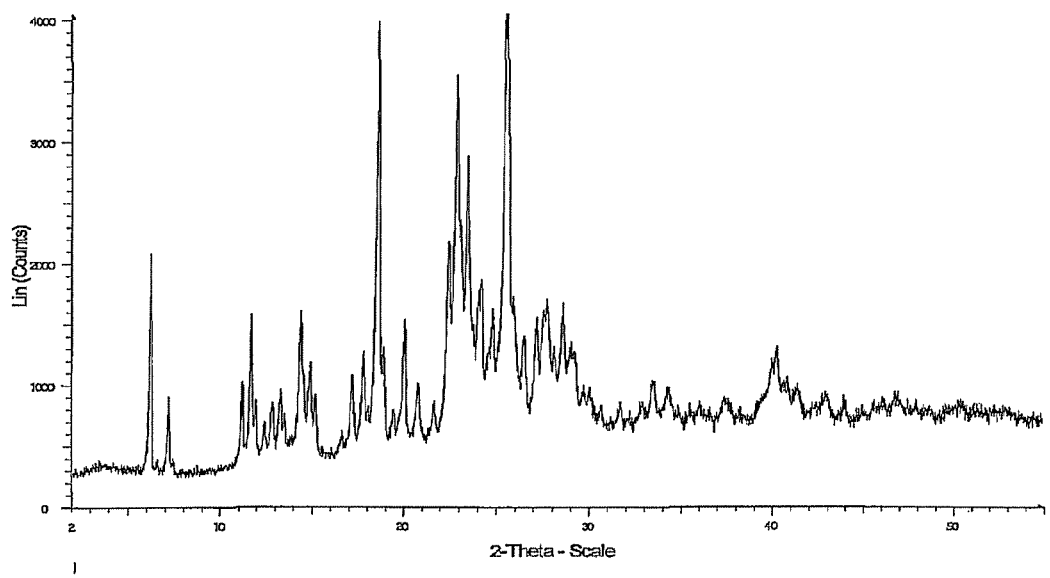
Figure 10: XRPD of afatinib dihydrochloride form A
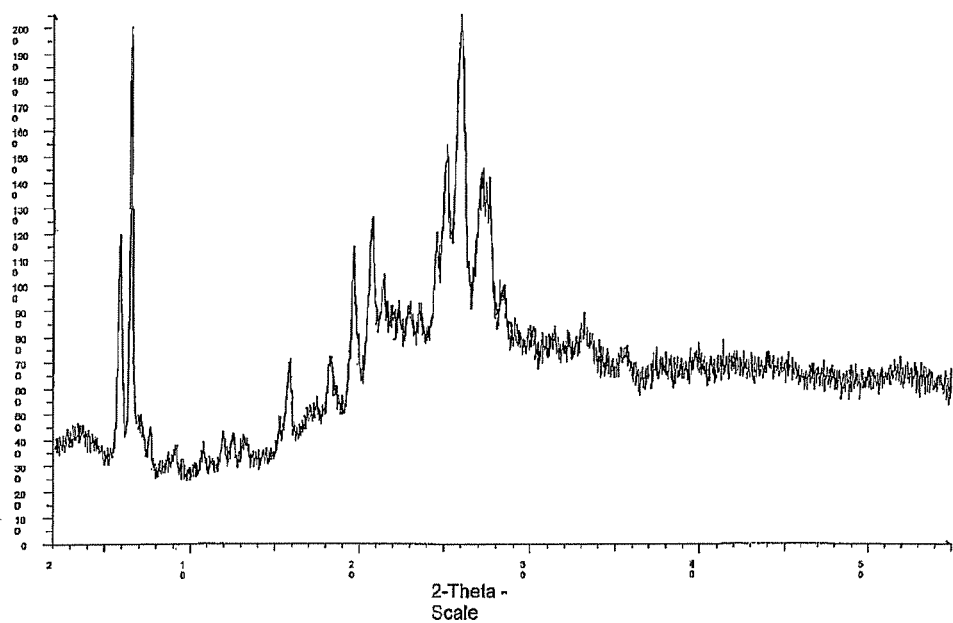

Figure 11: XRPD of afatinib dioxalate form A
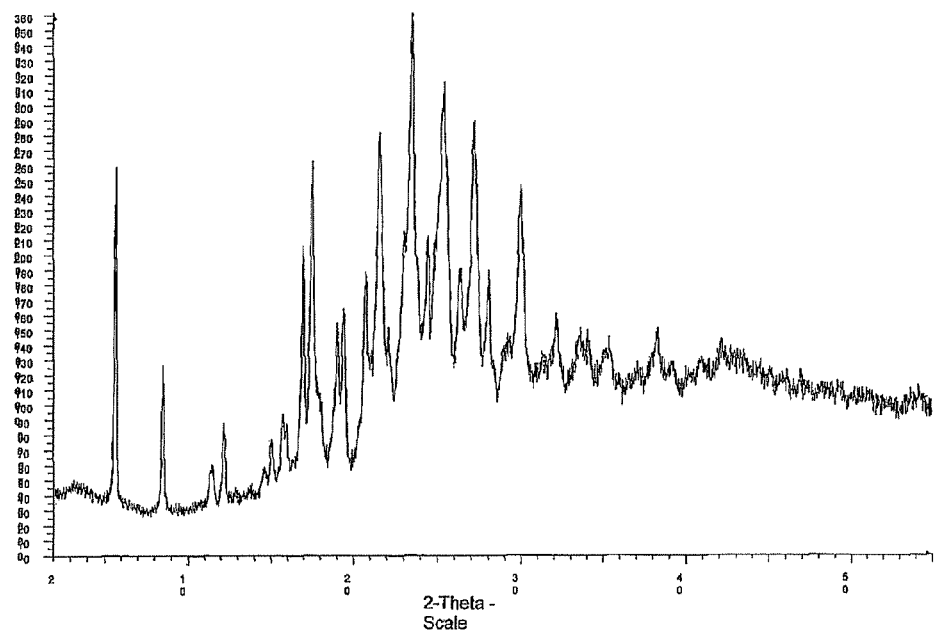
Figure 12: XRPD of afatinib dimesylate form A
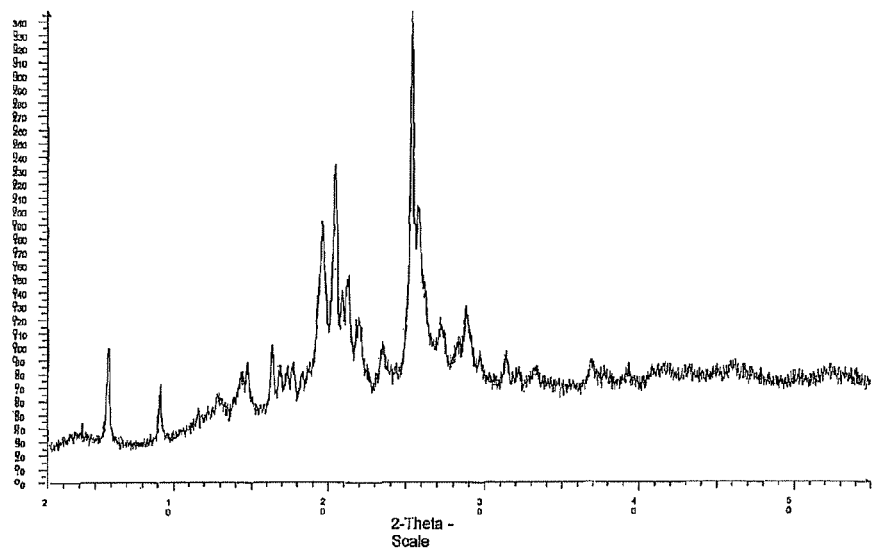

Figure 13: XRPD of afatinib dimesylate form B
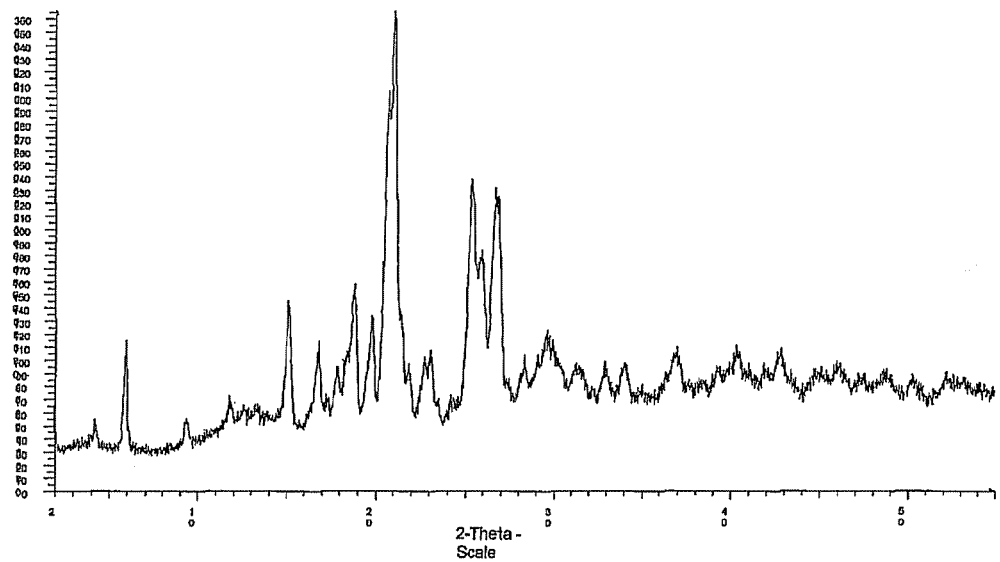
Figure 14: XRPD of afatinib diphosphate amorphous
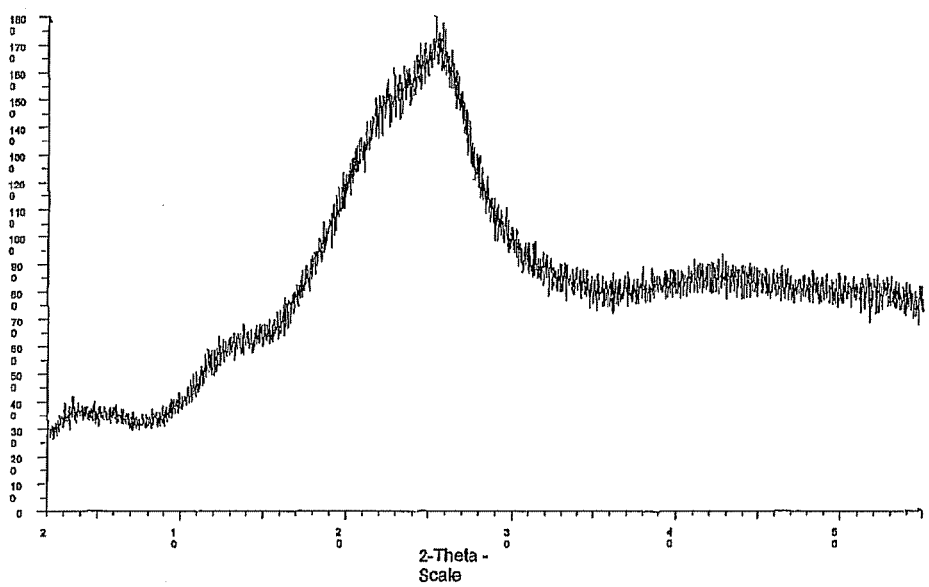

Figure 15: XRPD of afatinib diphosphate form A
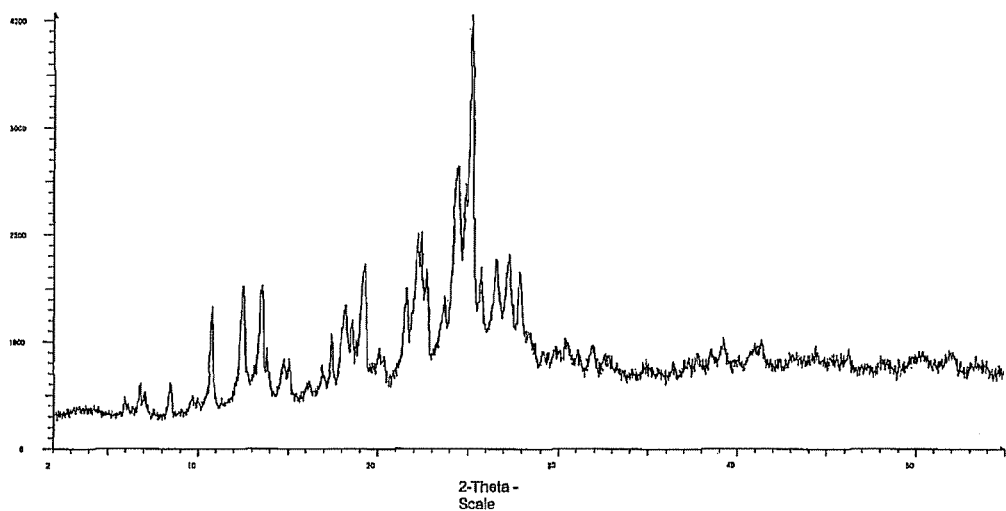
Figure 16: XRPD of afatinib di-L-malate amorphous
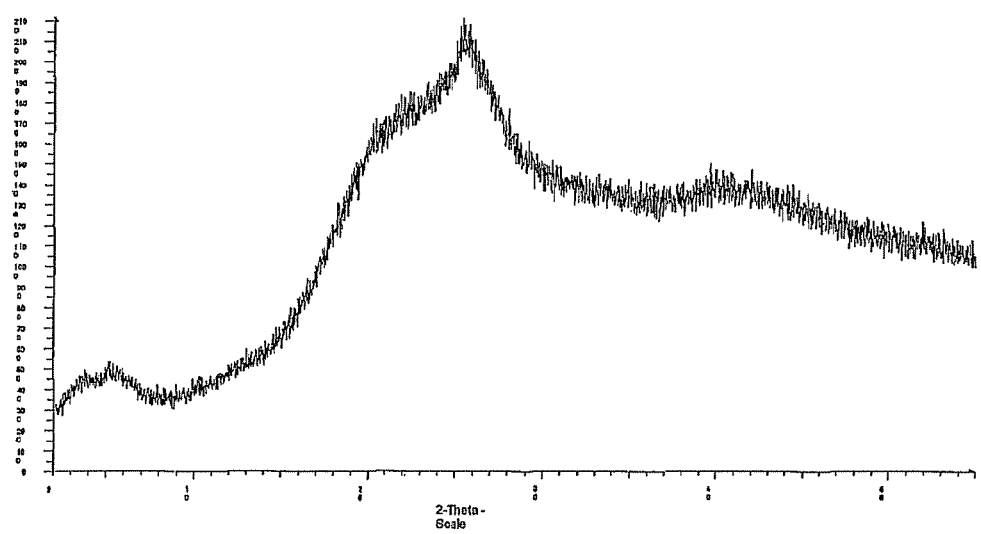

Figure 17: XRPD of afatinib citrate amorphous
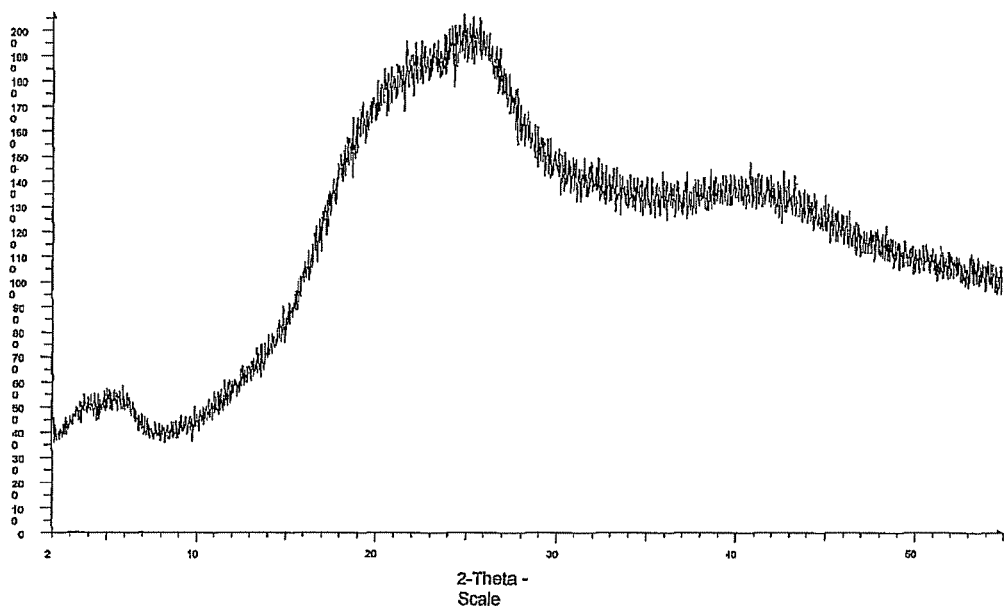
Figure 18: XRPD of afatinib disuccinate form A
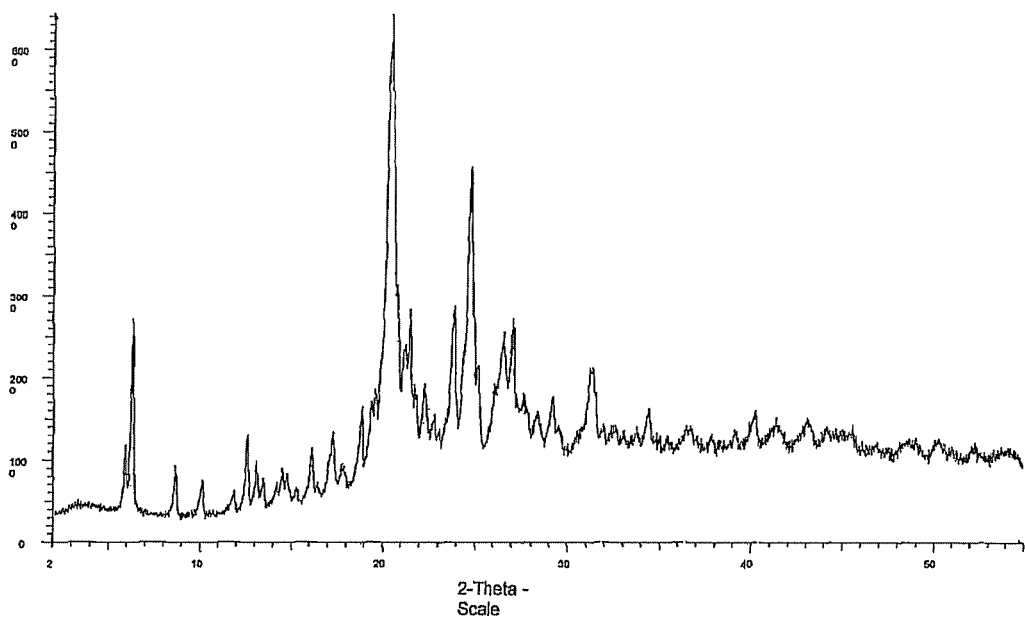

Figure 19: XRPD of afatinib L-aspartate form A
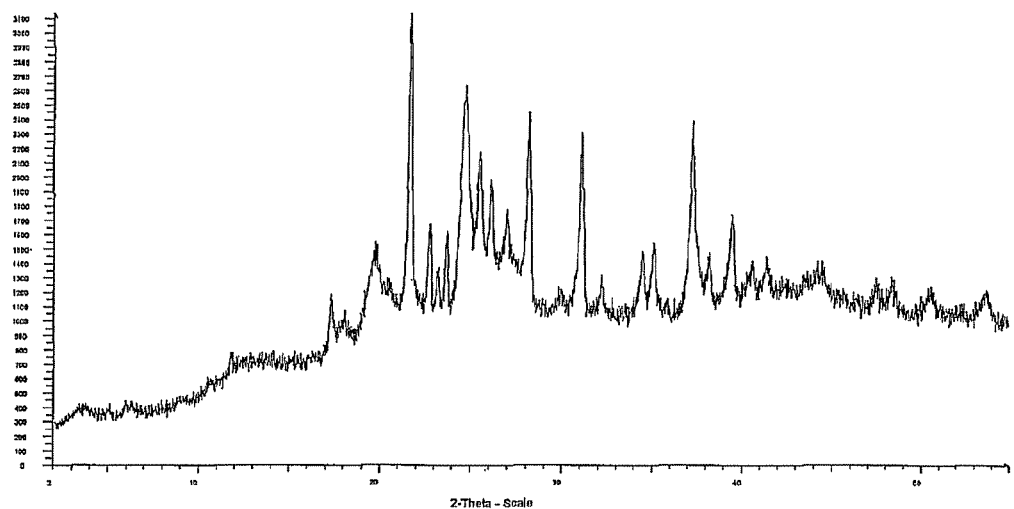
Figure 20: XRPD of Afatinib difumarate form A
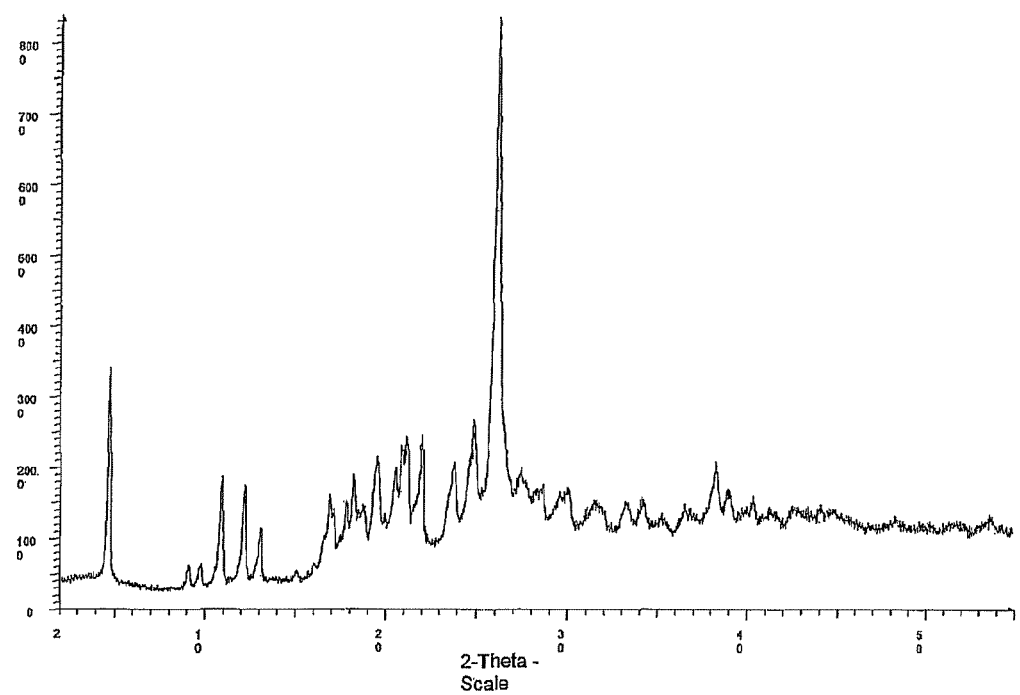

SALTS AND POLYMORPHIC FORMS OF AFATINIB

REFERENCE TO RELATED APPLICATIONS

This application is the U.S. National Phase of PCT/EP2011/62031 filed on Nov. 23, 2011, and claims the benefit of Indian Application No. 2807/DEL/2010, filed on Nov. 25, 2010.

FIELD OF THE INVENTION

The present invention relates to novel salts of Afatinib, crystalline forms thereof, crystalline forms of Afatinib and Afatinib di-maleate and a pharmaceutical composition comprising it, or said crystalline form thereof; and methods of preparing said Afatinib salt or said crystalline form thereof and said pharmaceutical composition.

BACKGROUND OF THE INVENTION

The compound, (E)-4-Dimethylamino-but-2-enoic acid {4-(3-chloro-4-fluorophenylamino)-7-[(S)-(tetrahydro-furan-3-yl)oxy]-quinazolin-6-yl}-amide, known as Afatinib, having the following structure:

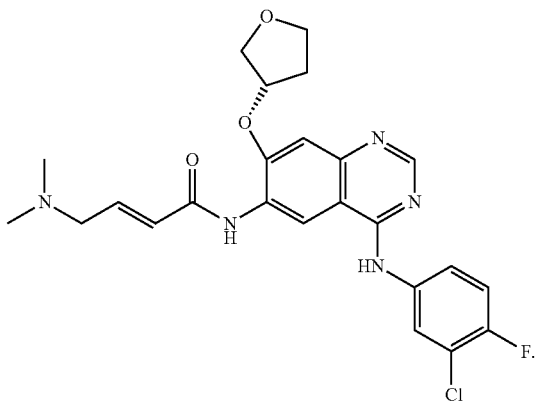

is an investigational orally administered irreversible inhibitor of both the epidermal growth factor receptor (EGFR) and human epidermal receptor 2 (HER2) tyrosine kinases. Afatinib is under development for treatment of several solid tumors including non-small cell lung cancer (NSCLC), breast, head and neck cancer, and a variety of other cancers.

Quinazoline derivatives, such as afatinib, are described in WO2002050043. This document also describes certain favourable pharmacological properties of this compound. The dimaleate salt and its crystalline form are described in WO2005037824.

Polymorphism, the occurrence of different crystal forms, is a property of some molecules and molecular complexes. A single molecule may give rise to a variety of polymorphs having distinct crystal structures and physical properties like melting point, thermal behaviors (e.g. measured by thermogravimetric analysis—"TGA", or differential scanning calorimetry—"DSC"), X-ray powder diffraction (XRPD or powder XRD) pattern, infrared absorption fingerprint, and solid state nuclear magnetic resonance (NMR) spectrum. One or more of these techniques may be used to distinguish different polymorphic forms of a compound.

Discovering new polymorphic forms and solvates of a pharmaceutical product can provide materials having desirable processing properties, such as ease of handling, ease of processing, storage stability, and ease of purification or as desirable intermediate crystal forms that facilitate conversion to other polymorphic forms. New polymorphic forms and solvates of a pharmaceutically useful compound or salts thereof can also provide an opportunity to improve the performance characteristics of a pharmaceutical product. It enlarges the repertoire of materials that a formulation scientist has available for formulation optimization, for example by providing a product with different properties, e.g., better processing or handling characteristics, improved dissolution profile, or improved shelf-life. For at least these reasons, there is a need for additional solid state forms of Afatinib free base and salts thereof.

SUMMARY OF THE INVENTION

The present invention provides crystalline forms of Afatinib free base, Afatinib di-maleate, processes for preparing them, and pharmaceutical compositions containing them. The present invention also provides Afatinib di-benzene sulphonate, Afatinib mono-fumarate, Afatinib di-fumarate, Afatinib di-sulphate, Afatinib di-hydrochloride, Afatinib di-oxalate, Afatinib di-mesylate, Afatinib di-phosphate, Afatinib di-l-malate, Afatinib di-succinate, Afatinib citrate and Afatinib l-aspartate. The present invention further provides crystalline forms of Afatinib di-benzene sulphonate, Afatinib mono-fumarate, Afatinib di-fumarate, Afatinib di-sulphate, Afatinib di-hydrochloride, Afatinib di-oxalate, Afatinib di-mesylate, Afatinib di-phosphate, Afatinib di-succinate, and Afatinib l-aspartate, processes for preparing them, and pharmaceutical compositions containing them.

The present invention further provides the use of the above described salts and crystalline forms for the preparation of Afatinib free base, Afatinib di-maleate, other salts of Afatinib and solid state forms thereof.

The present invention further provides a pharmaceutical composition comprising any one, or a combination of, the above described salts and crystalline forms, and at least one pharmaceutically acceptable excipient.

The present invention further provides the use of any one of the above described salts and crystalline forms disclosed herein for the treatment of cancer, particularly for the treatment of solid tumors including non-small cell lung cancer (NSCLC), breast, head and neck cancer, and a variety of other cancers.

The present invention also provides a method of treating cancer, comprising administering a therapeutically effective amount of at least one of the Afatinib or Afatinib di-maleate crystalline forms of the present invention, or at least one of the above pharmaceutical compositions to a person suffering from cancer, particularly a person suffering from solid tumors including but not limited to NSCLC, breast, head and neck cancer, and a variety of other cancers.

BRIEF DESCRIPTION OF THE DRAWINGS

FIG. 1 shows an X-ray powder diffractogram ("PXRD") pattern of crystalline Afatinib free base form, which may be designated form A.

FIG. 2 shows a PXRD pattern of crystalline Afatinib free base form, which may be designated form B.

FIG. 3 shows a PXRD pattern of crystalline Afatinib free base form, which may be designated form C.

FIG. 4: shows a PXRD pattern of crystalline Afatinib free base form, which may be designated form D.

FIG. 5: shows a PXRD pattern of crystalline Afatinib dimaleate form, which may be designated Afatinib dimaleate form B.

FIG. 6: shows a PXRD pattern of crystalline Afatinib dibenzenesulphonate form, which may be designated Afatinib dibenzenesulphonate form A FIG. 7: shows a PXRD pattern of crystalline Afatinib fumarate, which may be designated Afatinib fumarate form A.

FIG. 8: shows a PXRD pattern of crystalline Afatinib disulphate, which may be designated Afatinib disulphate form A.

FIG. 9: shows a PXRD pattern of crystalline Afatinib disulphate, which may be designated Afatinib disulphate form B.

FIG. 10: shows a PXRD pattern of crystalline Afatinib dihydrochloride, which may be designated Afatinib dihydrochloride form A.

FIG. 11: shows a PXRD pattern of crystalline Afatinib dioxalate, which may be designated Afatinib dioxalate form A.

FIG. 12: shows a PXRD pattern of crystalline Afatinib dimesylate, which may be designated Afatinib dimesylate form A.

FIG. 13: shows a PXRD pattern of crystalline Afatinib dimesylate, which may be designated Afatinib dimesylate form B.

FIG. 14: shows a PXRD pattern of amorphous Afatinib diphosphate.

FIG. 15: shows a PXRD pattern of crystalline Afatinib diphosphate, which may be designated Afatinib diphosphate form A.

FIG. 16: shows a PXRD pattern of amorphous Afatinib di-L-malate.

FIG. 17: shows a PXRD pattern of amorphous Afatinib citrate.

FIG. 18: shows a PXRD pattern of crystalline Afatinib disuccinate, which may be designated Afatinib disuccinate form A.

FIG. 19: shows a PXRD pattern of crystalline Afatinib L-aspartate, which may be designated Afatinib L-aspartate form A.

FIG. 20: shows a PXRD pattern of crystalline Afatinib difumarate, which may be designated Afatinib difumarate form A.

DETAILED DESCRIPTION OF THE INVENTION

The present invention relates to novel salts of Afatinib, to crystalline forms thereof, to crystalline forms of Afatinib and Afatinib di-maleate and to a pharmaceutical composition comprising it, or said crystalline form thereof; and to methods of preparing said Afatinib salt or said crystalline form thereof and said pharmaceutical composition.

A solid state may be referred to herein as being characterized by graphical data substantially "as depicted in" a Figure. Such data include, for example, powder X-ray diffractograms, FTIR spectra and solid state NMR spectra. The skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Afatinib or an Afatinib salt referred to herein as being characterized by graphical data "as depicted in" a Figure will thus be understood to include any crystal forms of Afatinib or Afatinib salt characterized with the graphical data having such small variations, as are well known to the skilled person, in comparison with the Figure.

A solid state may be referred to herein as polymorphically pure, or substantially free of any other crystalline (or polymorphic) forms of Afatinib or Afatinib salt of the invention. As used herein in this context, the expression "substantially free" will be understood to mean that the crystalline form contains 20% or less, 10% or less, 5% or less, 2% or less, or 1% or less of any other form of the subject compound as measured, for example, by PXRD. Thus, polymorphs of Afatinib or an Afatinib salt described herein as substantially free of any other polymorphic forms would be understood to contain greater than 80% (w/w), greater than 90% (w/w), greater than 95% (w/w), greater than 98% (w/w), or greater than 99% (w/w) of the subject polymorphic form of the Afatinib or Afatinib salt. Accordingly, in some embodiments of the invention, the described polymorphs of Afatinib or an Afatinib salt may contain from 1% to 20% (w/w), from 5% to 20% (w/w), from 5% to 10%, from 5% to 1% (w/w) or from 2% to 1% (w/w), preferably 1% (w/w) or less of one or more other crystal forms of Afatinib or an Afatinib salt.

The terms "XRPD" and "PXRD" are used interchangeably in the scientific literature by those skilled in the art of powder X-ray diffraction analysis, and the present application makes no distinction between these two expressions or their abbreviations.

As used herein, unless stated otherwise, the XRPD measurements are taken using copper Kα radiation wavelength λ=1.5406 Å.

A thing, e.g., a reaction mixture, may be characterized herein as being at, or allowed to come to "room temperature, often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

As used herein, the term "reduced pressure" refers to a pressure of about 10 mbar to about 50 mbar.

As used herein, the term "isolated" in reference to any of: Afatinib or an Afatinib salt or polymorphs thereof of the present invention and corresponds to said Afatinib or Afatinib salt polymorph that is physically separated from the reaction mixture where it was formed.

The present invention provides new crystalline forms of Afatinib or an Afatinib salt that have advantageous properties over other solid state forms of Afatinib or Afatinib salts, selected from at least one of: chemical purity, flowability, solubility, dissolution rate, morphology or crystal habit, stability, such as thermal and mechanical stability to polymorphic conversion, stability to dehydration and/or storage stability, low content of residual solvent, a lower degree of hygroscopicity, flowability, and advantageous processing and handling characteristics such as compressibility, and bulk density.

It is therefore an object of the present invention to provide new polymorphic forms of afatinib free base, as well as new pharmaceutically acceptable salts of afatinib and polymorphic forms thereof. Furthermore, pharmaceutical compositions comprising these novel forms, which do not encounter the above problems, are presented. In particular, the provided forms of afatinib show at least one of the following advantages compared to prior art forms of afatinib and afatinib salt: improved bioavailability, reduced inter-patient variability, improved overall therapeutic efficacy, good mechanical, polymorphic and/or chemical stability, excellent flow properties, good compressibility and improved dissolution profiles. The new forms are preferably non-hygroscopic and/or do not electrostatically charge. It has been found that the forms of afatinib and afatinib salts according to this invention are advantageous in at least one aspect of the above-mentioned properties.

Thus, the present invention relates to active pharmaceutical ingredients (hereinafter also referred to as "APIs"), selected from afatinib free base in polymorphic form A, afatinib free base in polymorphic form B, afatinib free base in polymorphic form C, afatinib free base in polymorphic form D and salts of the afatinib free base with one or more acid compounds of the formula $H_mX$, wherein H is a dissociable hydrogen atom, X is a pharmaceutically acceptable residue (i/e/ an anion of a pharmaceutically acceptable acid) and m is a natural number. Preferably, in the formula $H_mX$, X is not tartrate. Additionally when X is maleate or fumarate, then the afatinib salts are present in afatinib dimaleate form B or afatinib fumarate farm A as specified below.

In particular, the present invention relates to polymorphic forms A, B, C and D of afatinib free base as well as to the afatinib dimaleate form B and afatinib fumarate form A. Furthermore, it relates to the novel benzene sulphonate, sulphate, hydrochloride, oxalate, mesylate, phosphate, and malate salts of afatinib. Furthermore, the present invention relates to pharmaceutical compositions comprising the active pharmaceutical ingredient of the present invention, optionally together with at least a further active ingredient.

The APIs, in particular the salts of the present invention, contain the individual optical isomers, mixtures of the individual enantiomers or racemates of afatinib. Moreover, the present invention covers the new salts in any polymorphic form, including hydrates and/or solvates thereof and in any stoichiometry.

Preferably, in the above formula $H_mX$ of the inventive afatinib salts m is a number from 1 to 8, more preferably 1, 2, 3 or 4. more preferably, m is 1 or 2.

A summary of the preferred acid compounds for forming the salts and the corresponding $pK_a$ values is shown in Table A.

TABLE A

| Acid | $pK_{a1}$ | $pK_{a2}$ |
|---|---|---|
| Maleic acid | 1.93 | 6.58 |
| Fumaric acid | 3.03 | 4.44 |
| Benzenesulphonic acid | 0.7 | — |
| Sulphuric acid | −3 | 1.99 |
| Oxalic acid | 1.25 | 4.27 |
| Hydrochloric acid | −8 | — |
| Methanesulphonic acid | −2 | — |
| Phosphoric acid | 2.15 | 7.20 |
| L-Malic acid | 3.40 | 5.20 |
| Citric acid | 3.09 | 4.75 |
| Succinic acid | 4.2 | 5.6 |
| L-Aspartic acid | 2.10 | 3.86 |

In a further aspect of the invention, the invention pertains to an afatinib salt, wherein the acid compound is an organic acid with between 1 and 13 carbon atoms. Preferably, the organic acid has between 2 and 8 carbon atoms, atoms, preferably, between 3 and 5 and more preferably 4 carbon.

The APIs of the present invention, preferably the salts of the present invention, usually display a reduced hygroscopicity. Since these salts do not pull water as strongly as comparative salts in the art, they have advantages in galenic formulations.

In particular, the combination of the above described factors improves the standard tablet manufacturing process. The water content stability enables more uniform dosage units and an improved long-term shelf life of the formulations.

Suitable salts can be achieved with the following acids: Formic acid, dichloroacetic acid, glyoxylic acid, oxalic acid, acetic acid, glycolic acid, malonic acid, propanoic acid, lactic acid, maleic acid, succinic acid, malic acid, L-tartaric acid, L-aspartic acid, butanoic acid, glutaric acid, 2-oxoglutaric acid, L-glutamic acid, hippuric acid, 2-methylbutanoic acid, 3-methylbutanoic acid, pentanoic acid, picolinic acid, 3-pyridinecarboxylic acid, 4-pyridinecarboxylic acid, benzenesulfonic acid, L-ascorbic acid, citric acid, adipic acid, 3-methylglutaric acid, benzoic acid, 4-acet-amidobenzoic acid, hydroxybenzoic acid, dihydroxybenzoic acid, dihydroxymalic acid, gallic acid, 2,4,6-trihydroxybenzoic acid, aminobenzoic acid, heptanoic acid, D- or L-mandelic acid, octanoic acid, cinnamic acid, methylcinnamic acid, camphorsulfonic acid, camphor-10-sulfonic acid, cyclamic acid, dodecylsulfuric acid, 2-hydroxyethanesulfonic acid, L-glutamic acid, α-oxo glutaric acid, hydrobromic acid, napthalene-2-sulfonic acid, 1-hydroxy-2-napthoic acid, nitric acid, pamoic acid, phosphoric acid.

The inventive salt more preferably comprises an acid compound, which is one or more selected from the following list: Maleic acid, fumaric acid, benzenesulphonic acid, sulphuric acid, oxalic acid, hydrochloric acid, methanesulphonic acid, phosphoric acid, L-malic acid, citric acid, succinic acid and/or L-aspartic acid.

Preferably, the salt should not be formed of a tartaric acid, which may undergo polymorphic transitions and seems to lead to not desirable pharmaceutical formulations.

In a further aspect of the invention, generally the acid compound to afatinib free base compound ratio in the salt is from 1:3 to 3:1, preferably the ratio is from 1:2 to 2:1, more preferably from 1:1.5 to 1.5:1, in particular from 1:1 to 2:1.

In alternative embodiments, the invention relates to the hydrate and/or solvate forms of the inventive APIs, in particular of the inventive salts. The salts according to the invention, their hydrates and/or solvates generally exhibit the improved properties.

Preferably the inventive APIs, in particular the inventive salts, are in a crystalline form, or at least in a partly crystalline form. The higher degree of crystallinity leads to more stable salts of Afatinib. In addition, these salts display an improved flowability and formulation processability. Highly crystalline salts are less tacky and can be tabletted with high drug load uniformity. The high degree of crystallinity can be seen in XRD measurements and from the DCS graphs. Preferably the degree of crystallinity is more than or equal to 40 wt. %.

It is also preferred that the water content of the APIs of the present invention, in particular of the salts of the present invention, is less than 0.1 to 8 wt. %, more preferably from 0.5 to 5 wt. %, still more preferably from 0.8 to 3.5%. The water content is determined as described below in the experimental section. The APIs, in particular the salts according to the present invention, have high purity and a low residual solvent content. In cases where the solvent is not water, usually the solvent content is between 1 ppm and 3500 ppm, preferably less than 1500 ppm, more preferably less than 500 ppm, particularly less than 200 ppm.

Solvates and also hydrates of the APIs and/or salts according to the invention may be present, for example, as hemi-, mono-, di-, tri-, tetra-, penta-, hexa-solvates or hydrates, respectively. Solvents used for crystallisation, such as acetonitrile, alcohols, especially methanol, ethanol, aldehydes, ketones, especially acetone, esters, e.g. ethyl acetate, or alkanes, especially pentane, hexane, heptane or cyclohexane, may be embedded in the crystal grating.

The APIs and/or salts according to the invention preferably exist in isolated and essentially pure form, for example in a degree of purity of >95 wt. %, preferably >98 wt. %, more preferably >99 wt. %. The enantiomer purity of the salts according to the invention is >98 wt. %, preferably >99 wt. %.

Usually, pharmaceutically acceptable APIs of the present invention, in particular of the salts of afatinib, are obtained in crystalline form. Depending on the acidic compound, pharmaceutically acceptable salts of afatinib may, however, be obtained in different polymorphic forms. In crystalline solids with an identical chemical composition, the appearance of different resulting crystal gratings is termed polymorphism.

When the APIs and/or salts are subjected to differential scanning calorimetry (DSC), the endothermic peaks indicate molecular rearrangements or transformations. Moreover, none of the peaks in the figures shown below is related to residual solvents or other impurities.

The invention thus also relates to the polymorphic forms of the APIs and/or salts. Depending on the respective salt, the polymorphic forms show different properties, e.g., with regard to flowability and storage stability.

The inventive afatinib APIs, in particular the inventive afatinib salts, preferably are present in particulate form. Usually the particles have a volume mean particle size (D50) of 1 to 250 μm, preferably of 2 to 200 μm, more preferably of 5 to 150 μm, further more preferably of 10 to 120 μm, most preferably of 15 to 90 μm. The mean particle size is determined as described below in the experimental section. The afatinib salts of the invention preferably possess Hausner ratios in the range of 1.01 to 1.5 or 1.05 to 1.4, preferably of 1.06 to 1.3, more preferably from 1.08 to 1.25. The Hausner ratio is the ratio of tapped density to bulk density. Tapped and bulk density preferably are determined according to Ph. Eur. 6.0, 2.2.42.

In an alternatively preferred embodiment, the salts of the invention are formed in an amorphous state or form.

For the present application, the term "amorphous" usually relates to the condition of solid-state compounds, for which the constituents (atoms, ions or molecules) do not show a periodic arrangement over a larger scale (long-range order). However, in amorphous substances, the constituents are typically not completely stationary and are not in a purely statistical arrangement, but are instead distributed in such a way that they display a certain regularity and similarity to the crystalline condition with regard to the distance and orientation to their immediate neighbours (short range order). Amorphous substances thus generally display a short-range order, but no long-range order.

In contrast to anisotropic crystals, solid amorphous substances are isotropic. They typically do not have any well-defined melting point but instead slowly change into the fluid state by gradual softening. Amorphous substances can be distinguished from crystalline substances with the aid of X-ray diffraction, for which no sharp, but instead normally only few non-descript interferences at small diffraction angles are achieved.

Improved physicochemical properties are of importance when these salts are produced in the form of pharmaceutically active substances and when producing, storing and applying the galenic preparation. Due to an improved constancy of the physical parameters, an even higher quality of the formulations can be guaranteed.

In the following, preferred embodiments of the active pharmaceutical ingredients of the present invention are described in detail.

In one embodiment the invention relates to crystalline afatinib free base form A with an XRPD pattern showing characteristic peaks at 5.1, 24.3 and 24.6±0.2° 2-Theta.

Afatinib free base form A can be further characterised by an XRPD pattern having peaks at 3.9, 7.8, 18.7 and 20.6±0.2° 2-Theta.

Afatinib free base form A can alternatively be characterized by an XRPD pattern as shown in FIG. 1.

Afatinib free base form A may also be characterised by the XRPD peaks listed in the left column of Table 1 below. Optionally, Form A may be further characterised by the XRPD peaks listed in Table 1 below together with the corresponding relative intensity values.

TABLE 1

XRPD peak list of afatinib free base form A

| Angle 2-Theta ° [±0.2°] | Relative intensity % |
|---|---|
| 3.865 | 42.5 |
| 5.126 | 95.7 |
| 6.021 | 29.4 |
| 6.967 | 9.4 |
| 7.806 | 42.5 |
| 9.751 | 20.5 |
| 10.33 | 13.8 |
| 10.907 | 27.3 |
| 11.395 | 15.9 |
| 11.796 | 18.7 |
| 12.133 | 37.6 |
| 12.439 | 16.2 |
| 15.572 | 16.4 |
| 16.677 | 29.8 |
| 17.007 | 42.4 |
| 17.294 | 30.4 |
| 17.807 | 33.4 |
| 18.32 | 34.1 |
| 18.701 | 63.6 |
| 19.249 | 44.1 |
| 19.55 | 37.7 |
| 20.166 | 55.8 |
| 20.595 | 66.9 |
| 21.067 | 57.2 |
| 21.831 | 50 |
| 22.244 | 40.6 |
| 22.762 | 32.3 |
| 23.474 | 57 |
| 24.33 | 94.1 |
| 24.631 | 100 |
| 25.03 | 78.7 |
| 25.551 | 63.2 |
| 26.179 | 60.6 |
| 26.521 | 48.3 |
| 27.128 | 43.1 |
| 27.692 | 60.8 |
| 27.976 | 50.3 |
| 28.532 | 35.4 |
| 29.584 | 29.7 |
| 30.066 | 31.4 |
| 30.501 | 32.4 |
| 30.778 | 30.8 |

TABLE 1-continued

XRPD peak list of afatinib free base form A

| Angle 2-Theta ° [±0.2°] | Relative intensity % |
|---|---|
| 33.596 | 29.1 |
| 38.284 | 28.6 |
| 39.57 | 31.7 |
| 41.017 | 33.6 |

In one embodiment the invention relates to crystalline afatinib free base form B with an XRPD pattern showing characteristic peaks at 3.9, 7.8 and 24.3±0.2° 2-Theta.

Afatinib free base form B can be further characterised by an XRPD pattern having peaks at 20.6 and 24.6±0.2° 2-Theta.

Afatinib free base form B can alternatively be characterized by an XRPD pattern as shown in FIG. 2.

Afatinib free base form B may also be characterised by the XRPD peaks listed in the left column of Table 2 below. Optionally, Form B may be further characterised by the XRPD peaks listed in Table 2 below together with the corresponding relative intensity values.

TABLE 2

XRPD peak list of afatinib free base form B

| Angle 2-Theta ° [±0.2°] | Relative intensity % |
|---|---|
| 3.89 | 74.6 |
| 6.116 | 10.5 |
| 7.002 | 10.1 |
| 7.821 | 60.8 |
| 8.281 | 11.8 |
| 9.763 | 21.7 |
| 11.43 | 13.7 |
| 11.787 | 18.3 |
| 13.126 | 10.8 |
| 15.547 | 17 |
| 16.683 | 24 |
| 17.277 | 20.5 |
| 17.852 | 37.8 |
| 18.624 | 33.7 |
| 19.242 | 43 |
| 19.583 | 53 |
| 20.234 | 49.9 |
| 20.599 | 67.7 |
| 21.823 | 56.9 |
| 23.61 | 29.7 |
| 24.347 | 100 |
| 24.651 | 95.9 |
| 25.018 | 88.4 |
| 25.529 | 54.6 |
| 26.281 | 33.8 |
| 27.115 | 49.2 |
| 27.759 | 55.9 |
| 28.655 | 32.4 |
| 30.257 | 29.2 |
| 30.76 | 30.6 |
| 32.017 | 27.3 |
| 33.613 | 25.5 |
| 35.858 | 23.8 |
| 37.911 | 27.1 |
| 39.649 | 28.2 |

In one embodiment, the invention relates to crystalline afatinib free base form C with an XRPD pattern showing characteristic peaks at 5.1±0.2, 12.1±0.2 and 24.6±0.2° 2-Theta.

Afatinib free base form C can be further characterised by an XRPD pattern having peaks at 10.9, 17.0 and 21.0±0.2° 2-Theta.

Afatinib free base form C can alternatively be characterized by an XRPD pattern as shown in FIG. 3.

Afatinib free base form C may also be characterised by the XRPD peaks listed in the left column of Table 3 below. Optionally, Form C may be further characterised by the XRPD peaks listed in Table 3 below together with the corresponding relative intensity values.

TABLE 3

XRPD peak list of afatinib free base form C

| Angle 2-Theta ° [±0.2°] | Relative Intensity % |
|---|---|
| 5.106 | 100 |
| 5.975 | 3.7 |
| 7.469 | 6.8 |
| 9.436 | 2.4 |
| 10.304 | 8 |
| 10.894 | 12.7 |
| 11.221 | 3.5 |
| 11.71 | 5.8 |
| 12.071 | 20.2 |
| 14.073 | 2.7 |
| 16.509 | 15 |
| 16.975 | 28.9 |
| 17.623 | 6.6 |
| 18.213 | 13.4 |
| 18.668 | 8.9 |
| 19.022 | 21.3 |
| 19.468 | 6.6 |
| 20.073 | 11.9 |
| 21.003 | 25.9 |
| 21.974 | 11.5 |
| 22.25 | 11.2 |
| 22.642 | 9.3 |
| 23.314 | 13.6 |
| 24.316 | 18.4 |
| 24.607 | 26.4 |
| 25.514 | 11.3 |
| 26.111 | 28 |
| 26.434 | 15 |
| 27.594 | 15.4 |
| 27.994 | 7.9 |
| 28.445 | 7.6 |
| 28.818 | 7.6 |
| 30.486 | 8.7 |
| 32.215 | 7.3 |
| 33.443 | 7.9 |
| 33.974 | 7.8 |
| 35.869 | 7.6 |
| 36.872 | 8.7 |
| 38.083 | 8.9 |
| 38.803 | 8.9 |
| 39.498 | 7.8 |

In one embodiment, the invention relates to crystalline afatinib free base form D with an XRPD pattern showing characteristic peaks at 5.2±0.2, 6.0±0.2 and 18.7±0.2° 2-Theta.

Afatinib free base form D can be further characterised by an XRPD pattern having peaks at 21.1 and 23.5±0.2° 2-Theta.

Afatinib free base form D can alternatively be characterized by an XRPD pattern as shown in FIG. 4.

Afatinib free base form D may also be characterised by the XRPD peaks listed in the left column of Table 4 below. Optionally, Form D may be further characterised by the XRPD peaks listed in Table 4 below together with the corresponding relative intensity values.

TABLE 4

XRPD peak list of afatinib free base form D

| Angle 2-Theta ° [±0.2°] | Relative Intensity % |
|---|---|
| 5.166 | 76.3 |
| 6.026 | 87.9 |
| 7.526 | 8.5 |
| 10.386 | 10 |
| 10.826 | 26.9 |
| 12.117 | 29.1 |
| 12.419 | 19.3 |
| 13.267 | 11.3 |
| 16.188 | 17.5 |
| 16.57 | 22 |
| 17.076 | 33.6 |
| 17.381 | 27.1 |
| 18.716 | 100 |
| 19.086 | 29.6 |
| 20.144 | 34.4 |
| 21.06 | 48.5 |
| 22.108 | 34.8 |
| 22.848 | 29.3 |
| 23.516 | 65.9 |
| 24.481 | 45.1 |
| 25.071 | 35.9 |
| 25.427 | 46 |
| 25.62 | 49.4 |
| 26.124 | 35.2 |
| 26.645 | 31.1 |
| 27.409 | 36.1 |
| 27.95 | 43.4 |
| 29.548 | 34.3 |
| 29.942 | 29.9 |
| 30.384 | 22.3 |
| 31.91 | 19.8 |
| 32.578 | 20.3 |
| 34.356 | 18.7 |
| 35.458 | 24.4 |
| 37.444 | 19.4 |
| 39.529 | 22.8 |
| 40.827 | 23.5 |
| 40.921 | 22.6 |
| 41.668 | 24 |
| 48.161 | 19.9 |
| 50.217 | 20.9 |
| 53.199 | 18.5 |

In one embodiment, the invention relates to crystalline form B of the dimaleate salt of afatinib with an XRPD pattern showing characteristic peaks at 19.3±0.2, 22.1±0.2 and 25.6±0.2° 2-Theta.

Afatinib dimaleate form B can be characterized by an XRPD pattern having peaks at 18.8±0.2, 21.5±0.2, 25.1 and 29.1±0.2° 2-Theta.

Afatinib dimaleate form B of the dimaleate salt of afatinib can alternatively be characterized by an XRPD pattern as shown in FIG. 5.

Afatinib dimaleate form B may also be characterised by the XRPD peaks listed in the left column of Table 5 below. Optionally, Form B may be further characterised by the XRPD peaks listed in Table 5 below together with the corresponding relative intensity values.

TABLE 5

XRPD peak list of afatinib dimaleate form B

| Angle 2-Theta ° [±0.2°] | Relative Intensity % |
|---|---|
| 4.642 | 11.7 |
| 5.094 | 34.6 |
| 5.846 | 13.6 |
| 6.958 | 15.3 |
| 8.652 | 12.8 |
| 10.079 | 13 |
| 10.589 | 15.5 |
| 11.772 | 10 |
| 14.072 | 17.3 |
| 15.068 | 22.9 |
| 15.634 | 21.4 |
| 16.171 | 14.6 |
| 17.355 | 31.9 |
| 17.732 | 25.6 |
| 18.847 | 44.5 |
| 19.286 | 49.7 |
| 20.808 | 41 |
| 21.46 | 69.5 |
| 22.056 | 100 |
| 23.774 | 42.8 |
| 24.101 | 46.4 |
| 24.665 | 39.7 |
| 25.097 | 61.4 |
| 25.564 | 69.7 |
| 26.928 | 56.8 |
| 27.814 | 53.8 |
| 28.69 | 40.2 |
| 29.135 | 52.2 |
| 29.386 | 45.3 |
| 30.363 | 28.7 |
| 30.447 | 28.9 |
| 30.511 | 28.8 |
| 31.198 | 31.8 |
| 33.636 | 31.7 |
| 34.812 | 31.8 |
| 36.789 | 31.2 |
| 37.925 | 34.3 |
| 38.52 | 38.1 |

In one embodiment, the invention relates to the dibenzenesulphonate salt of afatinib. Preferably, the dibenzenesulphonate salt shows predominately amorphous character with an XRPD pattern showing no characteristic peaks.

The dibenzenesulphonate salt of afatinib can alternatively be characterized by an XRPD pattern as shown in FIG. 6.

In one embodiment, the invention relates to the monofumarate salt of afatinib. In a preferred embodiment the monofumarate salt is crystalline. In a further preferred embodiment crystalline afatinib monofumarate has an XRPD pattern showing characteristic peaks at 11.9±0.2, 19.4±0.2 and 24.7±0.2° 2-Theta. This form can be designated as afatinib monofumarate form A Afatinib monofumarate form A can be further characterised by an XRPD pattern having peaks at 7.0 and 21.3±0.2° 2-Theta.

Afatinib monofumarate form A can alternatively be characterized by an XRPD pattern as shown in FIG. 7.

Afatinib monofumarate form A may also be characterised by the XRPD peaks listed in the left column of Table 7 below. Optionally, Form A may be further characterised by the XRPD peaks listed in Table 7 below together with the corresponding relative intensity values.

TABLE 7

XRPD peak list of afatinib monofumarate salt

| Angle 2-Theta ° [±0.2°] | Relative intensity % |
|---|---|
| 4.577 | 12.5 |
| 6.971 | 24.2 |
| 7.297 | 15.6 |

TABLE 7-continued

XRPD peak list of afatinib monofumarate salt

| Angle 2-Theta ° [±0.2°] | Relative intensity % |
|---|---|
| 8.146 | 11.7 |
| 9.674 | 9.8 |
| 11.185 | 12.4 |
| 11.928 | 38.3 |
| 14.156 | 25.1 |
| 15.196 | 13.2 |
| 17.088 | 17.4 |
| 17.85 | 18.3 |
| 18.299 | 26.7 |
| 19.051 | 47.1 |
| 19.421 | 65.6 |
| 20.015 | 28.5 |
| 20.88 | 59.4 |
| 21.279 | 71.3 |
| 21.869 | 51.9 |
| 22.432 | 62.7 |
| 23.886 | 43.8 |
| 24.672 | 100 |
| 25.749 | 59.3 |
| 27.41 | 34.8 |
| 28.147 | 36.3 |
| 29.376 | 43.4 |
| 29.858 | 34.1 |
| 31.174 | 34.5 |
| 38.409 | 37.6 |

In one embodiment, the invention relates to the sulphate salt of afatinib. In a preferred embodiment the sulphate salt of afatinib is the crystalline. In a further preferred embodiment the crystalline afatinib sulphate salt has an XRPD pattern showing characteristic peaks at 20.4±0.2 and 25.6±0.2° 2-Theta. This form can be designated as afatinib disulphate form A.

Afatinib disulphate form A can be further characterized by an XRPD pattern having peaks at 21.3 and 22.3±0.2° 2-Theta.

Afatinib disulphate form A can alternatively be characterized by an XRPD pattern as shown in FIG. 8.

Afatinib disulphate form A may also be characterised by the XRPD peaks listed in the left column of Table 8 below. Optionally, Form A may be further characterised by the XRPD peaks listed in Table 8 below together with the corresponding relative intensity values.

TABLE 8

XRPD peak list of afatinib disulphate form A

| Angle 2-Theta ° [±0.2°] | Relative Intensity % |
|---|---|
| 5.147 | 13.4 |
| 5.919 | 16 |
| 6.531 | 13.2 |
| 8.097 | 9.6 |
| 10.383 | 10.4 |
| 11.895 | 23 |
| 12.592 | 16.8 |
| 13.821 | 16.2 |
| 14.662 | 22.8 |
| 15.144 | 18.8 |
| 15.882 | 16.3 |
| 16.306 | 24.4 |
| 16.876 | 20.3 |
| 17.494 | 23.9 |
| 18.344 | 28.7 |
| 19.418 | 23.9 |
| 20.112 | 36.2 |
| 20.38 | 53.4 |
| 21.252 | 39.9 |
| 22.323 | 37.5 |
| 22.943 | 32.3 |
| 23.942 | 32.2 |
| 24.595 | 39.2 |
| 25.245 | 61.7 |
| 25.574 | 100 |
| 26.915 | 44 |
| 27.274 | 38.2 |
| 27.967 | 45.3 |
| 28.488 | 37.4 |
| 29.317 | 35.6 |
| 31.067 | 28.4 |
| 32.953 | 30.7 |
| 37.111 | 23.9 |

In one embodiment, the invention relates to the sulphate salt of afatinib in the form of disulphate form B. In a preferred embodiment the afatinib disulphate form B has an XRPD pattern showing characteristic peaks at 6.1±0.2, 18.6±0.2 and 25.5±0.2° 2-Theta.

Afatinib disulphate form B can be further characterized by an XRPD pattern having peaks at 11.6±0.2, 14.3±0.2 and 22.8±0.2° 2-Theta.

Afatinib disulphate form B can alternatively be characterized by an XRPD pattern as shown in FIG. 9.

Afatinib disulphate form B may also be characterised by the XRPD peaks listed in the left column of Table 9 below. Optionally, Form B may be further characterised by the XRPD peaks listed in Table 9 below together with the corresponding relative intensity values.

TABLE 9

XRPD peak list of afatinib disulphate form B

| Angle 2-Theta ° [±0.2°] | Relative intensity % |
|---|---|
| 6.146 | 49.3 |
| 7.137 | 22.0 |
| 7.394 | 9.6 |
| 11.125 | 23.6 |
| 11.605 | 38.9 |
| 11.855 | 20.7 |
| 12.377 | 16.8 |
| 12.792 | 20.8 |
| 13.208 | 22.9 |
| 13.428 | 18.5 |
| 14.337 | 39.5 |
| 14.847 | 28.7 |
| 15.137 | 22.6 |
| 16.596 | 15.1 |
| 17.139 | 26.4 |
| 17.752 | 31.2 |
| 18.558 | 98.5 |
| 18.855 | 32.1 |
| 19.413 | 19.5 |
| 19.997 | 37.7 |
| 20.746 | 24.8 |
| 21.616 | 21.2 |
| 22.395 | 53.6 |
| 22.812 | 87.6 |
| 23.070 | 57.2 |
| 23.404 | 71.2 |
| 24.139 | 45.4 |
| 24.771 | 39.9 |
| 25.469 | 100.0 |
| 25.838 | 42.5 |
| 26.430 | 34.4 |
| 27.139 | 38.2 |
| 27.543 | 39.7 |
| 28.085 | 32.1 |
| 28.549 | 41.1 |

TABLE 9-continued

XRPD peak list of afatinib disulphate form B

| Angle 2-Theta ° [±0.2°] | Relative intensity % |
|---|---|
| 28.981 | 31.9 |
| 29.102 | 30.9 |
| 29.638 | 24.3 |
| 29.988 | 23.9 |
| 30.620 | 20.4 |
| 31.684 | 21.1 |
| 32.869 | 21.1 |
| 33.493 | 24.9 |
| 34.246 | 23.0 |
| 34.866 | 19.8 |
| 35.507 | 19.6 |
| 36.003 | 21.2 |
| 36.575 | 18.6 |
| 37.368 | 21.9 |
| 37.523 | 21.1 |
| 40.041 | 29.0 |
| 40.223 | 32.1 |
| 40.816 | 26.0 |
| 41.353 | 24.6 |
| 42.953 | 22.5 |
| 43.967 | 21.0 |
| 45.582 | 21.2 |
| 47.906 | 21.5 |
| 50.441 | 21.5 |

In one embodiment, the invention relates to the dihydrochloride salt of afatinib. In a preferred embodiment the dihydrochloride salt of afatinib is crystalline. In a further preferred embodiment the crystalline hydrochloride salt of afatinib has an XRPD pattern showing characteristic peaks at 5.8±0.2, 6.4±0.2 and 25.8±0.2° 2-Theta. This form can be designated as afatinib dihydrochloride salt form A.

Afatinib dihydrochloride salt form A can be further characterized by an XRPD pattern showing characteristic peaks at 19.5±0.2, 20.6±0.2, 25.0±0.2, and 27.1±0.2° 2-Theta.

Afatinib dihydrochloride salt form A can alternatively be characterized by an XRPD pattern as shown in FIG. 10.

Afatinib dihydrochloride salt form A may also be characterised by the XRPD peaks listed in the left column of Table 10 below. Optionally, Form A may be further characterised by the XRPD peaks listed in Table 10 below together with the corresponding relative intensity values.

TABLE 10

XRPD peak list of afatinib dihydrochloride form A

| Angle 2-Theta ° [±0.2°] | Relative intensity % |
|---|---|
| 5.769 | 58.3 |
| 6.434 | 97.7 |
| 7.009 | 24.3 |
| 7.525 | 21.8 |
| 9.027 | 18 |
| 10.668 | 18.9 |
| 11.859 | 20.7 |
| 12.426 | 20.4 |
| 13.209 | 18.9 |
| 15.188 | 23.6 |
| 15.776 | 33.6 |
| 17.371 | 25.6 |
| 18.199 | 34.5 |
| 19.538 | 55.9 |
| 20.629 | 61.3 |
| 21.333 | 49.8 |
| 21.87 | 44.7 |
| 22.29 | 45.8 |
| 22.914 | 43.4 |

TABLE 10-continued

XRPD peak list of afatinib dihydrochloride form A

| Angle 2-Theta ° [±0.2°] | Relative intensity % |
|---|---|
| 23.52 | 43.5 |
| 24.498 | 58.7 |
| 25.046 | 75.2 |
| 25.83 | 100 |
| 27.069 | 68.2 |
| 27.453 | 63.8 |
| 28.258 | 48.2 |
| 33.1 | 43.4 |

In one embodiment, the invention relates to the dioxalate salt of afatinib. In a preferred embodiment, the dioxalate salt of afatinib is crystalline. In a further preferred embodiment the crystalline dioxalate salt of afatinib has an XRPD pattern showing characteristic peaks at 5.6±0.2, 23.5±0.2 and 25.3±0.2° 2-Theta. This form can be designated as afatinib dioxalate salt form A.

Afatinib dioxalate salt form A can be further characterized by an XRPD pattern having peaks at 8.4±0.2, 17.4±0.2, 21.5±0.2, 29.9±0.2 and/or 32.1±0.2° 2-Theta.

Afatinib dioxalate salt form A can alternatively be characterized by an XRPD pattern as shown in FIG. 11.

Afatinib dioxalate salt form A may also be characterised by the XRPD peaks listed in the left column of Table 10b below. Optionally, Form A may be further characterised by the XRPD peaks listed in Table 10b below together with the corresponding relative intensity values.

TABLE 10b

XRPD peak list of afatinib dioxalate

| Angle 2-Theta ° [±0.2°] | Relative intensity % |
|---|---|
| 5.584 | 71.7 |
| 8.401 | 34.7 |
| 11.290 | 16.3 |
| 12.086 | 24.1 |
| 14.487 | 15.7 |
| 14.960 | 21.1 |
| 15.654 | 25.8 |
| 15.858 | 24.0 |
| 16.884 | 56.8 |
| 17.445 | 72.7 |
| 17.920 | 29.6 |
| 18.982 | 42.7 |
| 19.352 | 45.3 |
| 20.691 | 52.1 |
| 21.513 | 76.7 |
| 22.053 | 41.8 |
| 23.004 | 59.9 |
| 23.448 | 100.0 |
| 23.783 | 53.0 |
| 24.391 | 58.6 |
| 24.810 | 57.7 |
| 25.321 | 85.7 |
| 26.296 | 52.3 |
| 27.094 | 79.3 |
| 27.982 | 52.4 |
| 28.290 | 34.5 |
| 28.893 | 38.1 |
| 29.904 | 68.0 |
| 32.121 | 43.5 |
| 33.405 | 39.3 |
| 33.527 | 40.4 |
| 34.035 | 41.4 |
| 35.375 | 40.1 |
| 37.911 | 36.4 |
| 38.249 | 41.3 |

TABLE 10b-continued

XRPD peak list of afatinib dioxalate

| Angle 2-Theta °<br>[±0.2°] | Relative intensity<br>% |
|---|---|
| 39.143 | 35.5 |
| 40.122 | 33.4 |
| 40.885 | 36.3 |
| 42.178 | 39.5 |
| 45.049 | 34.4 |

In one embodiment, the invention relates to the dimesylate salt of afatinib. In a preferred embodiment the dimesylate salt of afatinib is crystalline. In a further preferred embodiment the crystalline dimesylate salt of afatinib has an XRPD pattern showing characteristic peaks at 19.5±0.2, 25.3±0.2 and 25.7±0.2° 2-Theta. This form can be designated as afatinib dimesylate salt form A.

Afatinib dimesylate salt form A can be further characterized by an XRPD pattern showing characteristic peaks at 5.7±0.2, 9.1±0.2, and 26.1±0.2° 2-Theta.

Afatinib dimesylate salt form A can alternatively be characterized by an XRPD pattern as shown in FIG. 12.

Afatinib dimesylate salt form A may also be characterised by the XRPD peaks listed in the left column of Table 12 below. Optionally, Form A may be further characterised by the XRPD peaks listed in Table 12 below together with the corresponding relative intensity values.

TABLE 12

XRPD peak list of afatinib dimesylate form A

| Angle 2-Theta °<br>[±0.2°] | Relative intensity<br>% |
|---|---|
| 5.717 | 28.2 |
| 9.077 | 20.6 |
| 11.503 | 15.5 |
| 12.766 | 18.5 |
| 14.282 | 23.2 |
| 14.655 | 25.2 |
| 16.283 | 29.1 |
| 16.801 | 24 |
| 17.289 | 23.8 |
| 17.628 | 24.6 |
| 18.24 | 23.2 |
| 18.696 | 25.1 |
| 19.544 | 55.2 |
| 20.386 | 67.5 |
| 20.835 | 40.5 |
| 21.212 | 43 |
| 21.922 | 34.7 |
| 22.434 | 24.9 |
| 23.431 | 29.4 |
| 24.266 | 24.8 |
| 24.879 | 32.3 |
| 25.291 | 100 |
| 25.716 | 58.5 |
| 26.115 | 41 |
| 27.166 | 34.8 |
| 28.735 | 37.2 |
| 29.617 | 27.7 |
| 31.302 | 27.4 |
| 32.152 | 24.2 |
| 33.27 | 23.4 |
| 36.888 | 25.7 |
| 46.188 | 25.7 |
| 46.724 | 24 |

In one embodiment, the invention relates to crystalline dimesylate salt of afatinib in form B. In a preferred embodiment the dimesylate salt of afatinib in form B has an XRPD pattern showing characteristic peaks at 15.0±0.2, 21.0±0.2 and 26.7±0.2° 2-Theta.

Afatinib dimesylate salt form B can be further characterized by an XRPD pattern having peaks at 4.1±0.2, 16.7±0.2 and 18.8±0.2° 2-Theta.

Afatinib dimesylate salt form B can alternatively be characterized by an XRPD pattern as shown in FIG. 13.

Afatinib dimesylate salt form B may also be characterised by the XRPD peaks listed in the left column of Table 13 below. Optionally, Form B may be further characterised by the XRPD peaks listed in Table 13 below together with the corresponding relative intensity values.

TABLE 13

XRPD peak list of afatinib dimesylate form B

| Angle 2-Theta °<br>[±0.2°] | Relative intensity<br>% |
|---|---|
| 4.127 | 14.6 |
| 5.850 | 31.1 |
| 9.261 | 14.9 |
| 11.738 | 19.6 |
| 13.219 | 16.9 |
| 15.040 | 39.4 |
| 16.696 | 30.9 |
| 17.228 | 19.0 |
| 17.806 | 25.7 |
| 18.358 | 28.9 |
| 18.746 | 41.7 |
| 19.685 | 36.4 |
| 20.642 | 83.4 |
| 20.956 | 100.0 |
| 21.400 | 36.2 |
| 21.787 | 26.3 |
| 22.669 | 27.7 |
| 23.033 | 27.6 |
| 23.440 | 18.6 |
| 24.147 | 19.7 |
| 24.375 | 18.4 |
| 25.308 | 64.8 |
| 25.861 | 49.9 |
| 26.681 | 61.7 |
| 27.263 | 22.6 |
| 28.081 | 24.5 |
| 28.266 | 28.2 |
| 29.017 | 28.2 |
| 29.540 | 33.3 |
| 29.838 | 30.3 |
| 31.210 | 26.3 |
| 31.334 | 25.7 |
| 31.404 | 25.9 |
| 31.575 | 25.0 |
| 32.186 | 20.8 |
| 32.875 | 26.9 |
| 34.014 | 25.7 |
| 36.745 | 28.3 |
| 36.854 | 28.7 |
| 39.210 | 25.6 |
| 40.263 | 30.2 |
| 41.899 | 25.1 |
| 42.748 | 27.9 |
| 43.328 | 23.9 |
| 50.196 | 23.2 |
| 52.160 | 24.5 |
| 54.074 | 22.4 |

In one embodiment, the invention relates to diphosphate salts of afatinib. In a preferred embodiment the diphosphate salt of afatinib is amorphous. The XRPD pattern of the diphosphate salt of afatinib in amorphous form is shown in FIG. 14.

In another preferred embodiment the diphosphate salt of afatinib is crystalline. In further preferred embodiment the crystalline diphosphate salt of afatinib has an XRPD pattern showing characteristic peaks at 10.7±0.2, 19.2±0.2 and 25.1±0.2° 2-Theta. This form can be designated as afatinib diphosphate salt form A.

Afatinib diphosphate salt form A can be further characterized by an XRPD pattern having peaks at 12.4±0.2, 13.4±0.2, 22.1±0.2 and 24.3±0.2° 2-Theta.

Afatinib diphosphate salt form A can alternatively be characterized by an XRPD pattern as shown in FIG. 15.

Afatinib diphosphate salt form A may also be characterised by the XRPD peaks listed in the left column of Table 15 below. Optionally, Form A may be further characterised by the XRPD peaks listed in Table 15 below together with the corresponding relative intensity values.

TABLE 15

XRPD peak list of afatinib diphosphate form A

| Angle 2-Theta °<br>[±0.2°] | Relative intensity<br>% |
|---|---|
| 5.843 | 11.4 |
| 6.696 | 14.1 |
| 6.954 | 12.6 |
| 8.370 | 14.8 |
| 9.546 | 11.8 |
| 10.654 | 32.3 |
| 12.430 | 37.1 |
| 13.444 | 37.2 |
| 13.780 | 22.9 |
| 14.699 | 20.2 |
| 14.992 | 20.3 |
| 16.118 | 15.2 |
| 16.853 | 18.8 |
| 17.360 | 26.1 |
| 18.110 | 33.0 |
| 18.492 | 29.3 |
| 19.148 | 42.3 |
| 20.034 | 22.9 |
| 20.285 | 20.8 |
| 21.511 | 36.7 |
| 22.138 | 49.1 |
| 22.312 | 48.0 |
| 22.627 | 41.0 |
| 23.653 | 34.3 |
| 24.359 | 63.9 |
| 24.809 | 60.8 |
| 25.140 | 100.0 |
| 25.670 | 41.6 |
| 26.525 | 43.2 |
| 27.204 | 44.4 |
| 27.833 | 40.1 |
| 28.358 | 26.6 |
| 29.109 | 21.5 |
| 29.801 | 23.1 |
| 30.381 | 24.4 |
| 31.077 | 22.5 |
| 31.894 | 23.3 |
| 32.541 | 21.4 |
| 36.382 | 19.6 |
| 37.768 | 21.7 |
| 38.505 | 22.3 |
| 39.184 | 25.2 |
| 41.336 | 24.7 |
| 44.419 | 21.9 |
| 46.219 | 22.9 |
| 49.059 | 19.0 |
| 49.796 | 20.8 |
| 49.825 | 21.1 |
| 52.109 | 21.8 |

In one embodiment, the invention relates to di-L-malate salts of afatinib. In a preferred embodiment the di-L-malate salt of afatinib is amorphous. The XRPD pattern of the di-L-malate salt of afatinib in amorphous form is shown in FIG. 16.

In one embodiment the invention relates to citrate salts of afatinib. In a preferred embodiment the citrate salt of afatinib is amorphous. The XRPD pattern of the citrate salt of afatinib in amorphous form is shown in FIG. 17.

In one embodiment, the invention relates to disuccinate salts of afatinib. In a preferred embodiment the disuccinate salt of afatinib is crystalline. In a preferred embodiment the crystalline disuccinate salt of afatinib has an XRPD pattern showing characteristic peaks at 6.2±0.2, 20.3±0.2 and 24.7±0.2° 2-Theta. This form can be designated as afatinib disuccinate salt form A.

Afatinib disuccinate salt form A can be further characterized by an XRPD pattern having peaks at 21.4±0.2, 23.8±0.2 and 31.3±0.2° 2-Theta.

Afatinib disuccinate salt form A can alternatively be characterized by an XRPD pattern as shown in FIG. 18.

Afatinib disuccinate salt form A may also be characterised by the XRPD peaks listed in the left column of Table 18 below. Optionally, Form A may be further characterised by the XRPD peaks listed in Table 18 below together with the corresponding relative intensity values.

TABLE 18

XRPD peak list of afatinib disuccinate form A

| Angle 2-Theta °<br>[±0.2°] | Relative intensity<br>% |
|---|---|
| 5.835 | 18.1 |
| 6.207 | 42.1 |
| 8.538 | 14.3 |
| 9.993 | 11.3 |
| 11.758 | 9.4 |
| 12.494 | 19.9 |
| 13.03 | 15 |
| 13.364 | 11.8 |
| 14.114 | 11.1 |
| 14.394 | 13.7 |
| 14.65 | 12.8 |
| 15.184 | 9.5 |
| 16.068 | 17.4 |
| 16.354 | 10.8 |
| 17.212 | 20.6 |
| 17.723 | 14.2 |
| 18.775 | 25.3 |
| 19.323 | 25.9 |
| 19.506 | 28.5 |
| 20.349 | 100 |
| 20.756 | 48 |
| 21.123 | 37 |
| 21.395 | 43.8 |
| 21.677 | 29.6 |
| 22.183 | 29.9 |
| 22.691 | 23.9 |
| 22.948 | 20.6 |
| 23.314 | 23.3 |
| 23.784 | 43.7 |
| 24.27 | 33.5 |
| 24.663 | 70.9 |
| 25.096 | 33.2 |
| 26.045 | 29.7 |
| 26.475 | 39.7 |
| 26.984 | 42.1 |
| 27.518 | 28 |
| 28.29 | 24.5 |
| 29.117 | 27.2 |
| 29.438 | 21.9 |
| 30.517 | 20.5 |
| 31.27 | 32.2 |
| 31.879 | 22.1 |
| 32.344 | 21.7 |
| 32.533 | 21.9 |
| 33.025 | 20.1 |
| 33.745 | 21.7 |
| 34.371 | 25.1 |
| 34.858 | 19.1 |
| 35.373 | 19.9 |
| 36.444 | 21.7 |
| 36.689 | 21.6 |
| 37.805 | 19.9 |
| 39.157 | 20.6 |
| 40.016 | 22.4 |
| 40.201 | 24.5 |

TABLE 18-continued

XRPD peak list of afatinib disuccinate form A

| Angle 2-Theta °<br>[±0.2°] | Relative intensity<br>% |
|---|---|
| 41.353 | 23.4 |
| 43.099 | 23.3 |
| 45.546 | 22 |
| 46.874 | 18.5 |
| 47.466 | 17.7 |
| 50.208 | 19 |
| 50.312 | 19.3 |
| 52.319 | 18.6 |

In one embodiment the invention relates to L-aspartate salts of afatinib. In a preferred embodiment the L-aspartate salt of afatinib is crystalline. In a further preferred embodiment the L-aspartate salt of afatinib has an XRPD pattern showing characteristic peaks at 21.6±0.2, 31.0±0.2 and 37.2±0.2° 2-Theta. This form can be designated as afatinib L-aspartate salt form A.

Afatinib L-aspartate salt form A can be further characterized by an XRPD pattern having peaks at 24.6±0.2, 28.1 1 0.2, and 39.4±0.2° 2-Theta.

Afatinib L-aspartate salt form A can alternatively be characterized by an XRPD pattern of the L-aspartate salt of afatinib in form A is shown in FIG. 19.

Afatinib L-aspartate salt form A may also be characterised by the XRPD peaks listed in the left column of Table 19 below. Optionally, Form A may be further characterised by the XRPD peaks listed in Table 19 below together with the corresponding relative intensity values.

TABLE 19

XRPD peak list for afatinib L-aspartate form A

| Angle 2-Theta °<br>[±0.2°] | Relative intensity<br>% |
|---|---|
| 4.906 | 11.8 |
| 5.870 | 13.9 |
| 10.583 | 18.7 |
| 11.712 | 24.5 |
| 17.270 | 36.5 |
| 19.698 | 49.3 |
| 21.574 | 100.0 |
| 22.668 | 53.3 |
| 23.146 | 42.6 |
| 23.607 | 51.8 |
| 24.608 | 84.1 |
| 25.420 | 69.4 |
| 26.052 | 63.0 |
| 26.876 | 56.7 |
| 28.101 | 78.0 |
| 29.892 | 38.6 |
| 31.011 | 73.7 |
| 32.150 | 41.9 |
| 34.391 | 47.1 |
| 35.011 | 49.1 |
| 35.754 | 36.4 |
| 37.174 | 76.2 |
| 38.111 | 45.4 |
| 39.387 | 55.3 |
| 40.529 | 44.9 |
| 41.332 | 44.1 |
| 44.423 | 42.8 |
| 47.472 | 39.8 |
| 48.283 | 41.4 |
| 50.525 | 39.3 |
| 53.707 | 38.5 |

In one embodiment, the invention relates to the difumarate salt of afatinib. In a preferred embodiment the difumarate salt of afatinib is crystalline. In a further preferred embodiment crystalline afatinib difumarate has an XRPD pattern showing characteristic peaks at 4.6±0.2, 24.8±0.2 and 26.1±0.2° 2-Theta. This form can be designated as afatinib difumarate salt form A.

Afatinib difumarate salt form A can be further characterized by an XRPD pattern showing characteristic peaks at 10.8±0.2 and 19.5±0.2° 2-Theta.

Afatinib difumarate salt form A can alternatively be characterized by an XRPD pattern as shown in FIG. 20.

Afatinib difumarate salt form A may also be characterised by the XRPD peaks listed in the left column of Table 20 below. Optionally, Form A may be further characterised by the XRPD peaks listed in Table 20 below together with the corresponding relative intensity values.

TABLE 20

XRPD peak list for afatinib difumarate form A

| Angle 2-Theta °<br>[±0.2°] | Relative intensity<br>% |
|---|---|
| 4.631 | 40.6 |
| 9.028 | 7.1 |
| 9.675 | 7.2 |
| 10.845 | 22.1 |
| 12.120 | 20.6 |
| 13.021 | 13.3 |
| 15.046 | 6.1 |
| 16.020 | 7.5 |
| 16.563 | 12.2 |
| 16.859 | 19.1 |
| 17.064 | 15.6 |
| 17.767 | 17.9 |
| 18.167 | 22.4 |
| 18.722 | 16.9 |
| 19.479 | 25.5 |
| 20.493 | 23.7 |
| 20.857 | 27.5 |
| 21.126 | 28.8 |
| 21.957 | 28.3 |
| 23.418 | 19.3 |
| 23.726 | 24.4 |
| 24.584 | 25.3 |
| 24.830 | 31.8 |
| 26.081 | 100.0 |
| 26.480 | 30.0 |
| 27.352 | 23.0 |
| 27.628 | 21.4 |
| 28.237 | 19.7 |
| 28.563 | 20.4 |
| 29.264 | 17.4 |
| 29.542 | 19.5 |
| 29.955 | 20.3 |
| 31.108 | 16.9 |
| 31.490 | 17.9 |
| 33.022 | 16.0 |
| 33.237 | 17.7 |
| 34.187 | 18.3 |
| 35.304 | 14.6 |
| 36.501 | 17.6 |
| 38.248 | 24.7 |
| 38.957 | 19.9 |
| 40.355 | 18.8 |
| 41.547 | 16.0 |
| 42.618 | 17.0 |
| 44.071 | 16.6 |
| 44.853 | 16.2 |
| 48.292 | 15.3 |
| 53.702 | 15.1 |

Further, it is an object of the present invention to provide an improved process for producing afatinib in the form of different pharmaceutically acceptable salts, which show a constant dissolution profile before and after storage. The present invention surprisingly affords a process for the manufacture of the inventive salt as described above in a form, which is at least partially crystalline, characterized in that:
(i) the free base compound and/or the corresponding acid compound is dissolved in an organic solvent,
(ii) the solution or solutions of (i) are mixed with each other, or alternatively with the other compound of either the free base compound or the corresponding acid compound, whichever was not originally dissolved in step (i),
(iii) optionally, the solution of (ii) is stirred, preferably for at least 5 minutes,
(iv) the solution is kept without stirring under conditions acceptable for salt crystallization, such as at RTP, with or without heating, cooling, reduced pressure, and/or vacuum, preferably for at least 1 hour, but more preferably for at least 1 day,
(v) the salt is separated and dried, e.g. by decantation of the supernatant or filtration, followed by drying, optionally under vacuum.

The term "RTP" stands for ambient room temperature and pressure and preferably refers to a temperature of about 23° C. and a pressure of about 1013 mbar.

In the dissolving process (i), the organic solvent employed is advantageously an alcohol, such as ethanol or isopropanol, or an alkylnitrile, especially acetonitrile, and/or water. The solvent may be warmed to above room temperature to e.g. 25 to 60° C., more preferably 30 to 50° C., most preferably 40 to 45° C.

The use of solvents, having undesirable toxic effects, is thus avoided.

In the process step (ii), the aqueous solution employed is advantageously a 10 to 30 wt. %, more preferably a 15 to 25 wt. %, such as a 20 wt. % solution of the acid compound. The stirring step can be preferably from 5 to 60 minutes, more preferably it is from 7 to 15 minutes.

In the process step (iv) the solution is advantageously left standing, so as to slowly evaporate off the solvent. This is preferably conducted by cooling to room temperature or below, more preferably cooling to −10 to +25° C., still more preferably −5 to +10° C., most preferably 0 to 5° C. The concentration of the solution can also take place by warming to above room temperature, e.g. to higher than 25 to 100° C., more preferably 30 to 70° C.

In the process step (v) the drying is preferably effected at elevated temperatures, more preferably at 20 to 50° C. most preferably at 30 to 42° C. This step is preferably conducted under vacuum. The term "vacuum" usually indicates that the pressure is preferably selected to be 1 to 100 mbar, preferably 10 to 50 mbar, more preferably 20 to 40 mbar, such as 30 mbar. The drying typically takes place until a constant mass is obtained. Depending on the drying conditions, the drying may take from 1 to 48 h, preferably 1.5 to 24 h, such as 2 to 10 h.

In a preferred variant, the crystallisation may be optimized, e.g. accelerated, by adding at least one seed crystal.

The invention also relates in particular to a pharmaceutical composition, especially in a solid dosage form, comprising an inventive API, in particular, comprising an inventive afatinib salt as described above, preferably for oral administration, optionally together with one or more pharmaceutically acceptable excipients and/or additives.

The present invention further provides the use of the above described salts and crystalline forms for the preparation of Afatinib free base, Afatinib di-maleate, other afatinib salts and solid state forms thereof. e.g. by conversion of the above described salts and crystalline forms to Afatinib free base, Afatinib di-maleate, other Afatinib salts and solid state forms thereof, and optionally further preparing a pharmaceutical formulation of the resulting Afatinib free base, Afatinib di-maleate, other Afatinib salt and solid state forms thereof.

The present invention further provides a pharmaceutical composition comprising any one, or a combination of, the above described salts and crystalline forms, and at least one pharmaceutically acceptable excipient.

The present invention further provides the use of any one of the above described salts and crystalline forms disclosed herein for the treatment of cancer, particularly for the treatment of solid tumors including NSCLC, breast, head and neck cancer, and a variety of other cancers.

The present invention also provides a method of treating cancer, comprising administering a therapeutically effective amount of at least one of the Afatinib or Afatinib di-maleate crystalline forms of the present invention, or at least one of the above pharmaceutical compositions to a person suffering from cancer, particularly a person suffering from solid tumors including but not limited to NSCLC, breast, head and neck cancer, and a variety of other cancers.

A further aspect of the present invention relates to a pharmaceutical composition comprising the API of the present invention, in particular, the afatinib salt of the present invention, and at least one further active pharmaceutical ingredient. Preferably, the at least one further active pharmaceutical ingredient is selected from e.g. paclitaxel, cis-platin, pemetrexed, vinorelbine, simvastatin, letrozole, intedanib, bevacizumab, temozolomide, rapamycin, herceptin and cetuximab, as well as pharmaceutically acceptable salts thereof. Unexpectedly, such a composition shows superior properties.

The pharmaceutical composition comprising the API of the present invention ($\alpha$), in particular, the afatinib salt of the present invention and at least one further active pharmaceutical ingredient ($\beta$) shows superior pharmacologic properties. In particular, the combination of the components ($\alpha$) and ($\beta$) shows an unexpected additive or even synergistic effect. Especially, the combination of components ($\alpha$) and ($\beta$) shows an unexpected superior effect in the treatment of cancer, immune disorders, respiratory and/or gastrointestinal diseases.

Specific cancers and immune disorders include, but are not limited to, advanced malignancy, amyloidosis, neuroblastoma, meningioma, hemangiopericytoma, multiple brain metastases, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-cell lymphoma, cutaneous B-cell lymphoma, diffuse large B-cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, leiomyoma, resistant and refractory multiple myeloma, myelofibrosis, sickle cell anemia and myelodysplastic syndrome.

Administration of the API of the present invention (α), in particular the afatinib salt of the present invention and at least one further active pharmaceutical ingredient (β) to a patient, can occur simultaneously or sequentially by the same or different routes of administration. The compounds can be administered orally, intravenously, subcutaneously and/or intramuscularly. A preferred route of administration for the API of the present invention (α), in particular the afatinib salt of the present invention and at least one further active pharmaceutical ingredient (β) is orally. Preferably, the API of the present invention (α), in particular the afatinib salt of the present invention and at least one further active pharmaceutical ingredient (β) are administered simultaneously, more preferably in a single dosage form, still more preferably in a single solid oral dosage form, e.g. a tablet or a capsule, whereas a tablet is preferred.

In one embodiment, the API of the present invention (α), in particular the afatinib salt of the present invention, can be administered daily in an amount of from about 10 to about 150 mg, preferably from about 20 to about 60 mg, more preferably from about 20 to about 50 mg and most preferably in an amount of 40 mg, whereas the further active pharmaceutical ingredient (β) can be administered in an amount of from about 0.01 to about 350 mg, preferably from about 0.1 to about 250 mg, more preferably from about 0.5 to about 150 mg and most preferably in an amount of 1.0 to 100 mg.

In another preferred embodiment, the API of the present invention (α), in particular the afatinib salt of the present invention and at least one further active pharmaceutical ingredient (β), may be administered in a single daily dose or in divided doses two to six times a day. In certain embodiments of the invention, the API of the present invention (α), in particular the afatinib salt of the present invention and at least one further active pharmaceutical ingredient (β), may be administered less frequent then once daily, e.g. every second, third, fourth, fifth, sixth or seventh day. Preferably, the pharmaceutical composition, comprising the API of the present invention (α), in particular the afatinib salt of the present invention, and at least one further active pharmaceutical ingredient (β) is applied once daily, once weekly, twice weekly or thrice weekly.

In certain embodiments, the API of the present invention (α), in particular the afatinib salt of the present invention and at least one further active pharmaceutical ingredient (β) are cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

Consequently, in one specific embodiment of the invention, the API of the present invention (α), in particular the afatinib salt of the present invention and at least one further active pharmaceutical ingredient (β), are administered in a three to six week cycle with a rest period of about a week or two weeks, preferably in a three week cycle with a rest period of one week. The invention further allows the frequency, number, and length of dosing cycles to be increased.

In one embodiment, the API of the present invention (α), in particular the afatinib salt of the present invention and at least one further active pharmaceutical ingredient (β), are administered daily and continuously for three or four weeks, followed by a break of one or two weeks.

The invention shall be illustrated by the following examples, which should not be construed as limiting.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

List of Equipment

XRD:
Samples were analysed on a Bruker AXS D8 Advance powder X-ray diffractometer; measurement conditions were as follows:

| | |
|---|---|
| radiation | Cu Kα |
| | λ = 1.5406 Å |
| source | 38 kV / 40 mA |
| detector | Vantec-1 |
| detector slit | 10.39 mm |
| detector antiscattering slit | 6.17 mm |
| divergence slit | v6.00 |
| antiscattering slit | 0.5° |
| 2θ range | 2° ≤ 2θ ≤ 55° |
| step size | 0.017° |
| step time | 0.2 s |

Residual Water Content:
determined according to the Karl Fischer method as described in Ph. Eur. 6. edition, 2008, section 2.5.12. The determination is done using Mettler Toledo DL31 Karl Fischer titrator. Usually, a sample of 50 to 100 mg of the salt is analyzed.

IR:
Perkin Elmer model Spectrum One FT IR in diffuse reflectance mode.

DSC:
Mettler Toledo Model DSC 822; heating range for the samples 30 to 300 deg C.; heating rate=10 deg C./min; purge gas=nitrogen 50 ml/min; 40 micron aluminum crucible.

Melting Point:
Lab India Visual melting range apparatus; particle sizes: the volume mean particle size (D50) is determined by the light scattering method, using a Mastersizer 2000 apparatus made by Malvern Instruments (wet measurement, 2000 rpm, ultrasonic waves for 60 sec., data interpretation via Fraunhofer method).

Determination of Residual Solvent
a) GC Chromatographic Conditions

| | |
|---|---|
| Instrument | Agilent Gas Chromatograph (6890N) equipped with Gerstel Multi Purpose Sampler MPS2 |
| Column | DB-624, 30 M x 0.53 mm, of 3.0 μm |
| Injector | 180° C., Split Ratio 3:1, Total flow: 10.4 ml/min |
| Carrier gas | Nitrogen @ 2.0 ml/min [(constant flow), (Eq. Pressure: 1.45 psi)] |
| Oven | 40° C. (hold for 15 min), Ramp 10° C./min up to 160° C. (hold for 5 min) |
| Detector | FID @ 200° C. |
| Hydrogen | @ 30.0 ml/min |
| Air | @ 300.0 ml/min |

-continued

| | |
|---|---|
| Make up flow | 28 ml/min |
| Quantity of sample | 100 mg |
| Solvent for dissolving | N,N-dimethylformamide | b) Head Space Parameters

| Agitator Parameters | |
|---|---|
| Incubation temp. | 85° C. |
| Incubation time | 15 min |
| Agitator speed | 500 rpm |
| Agitator on time | 3 s |
| Agitator off time | 3 s |
| Syringe Setting | |
| Syringe temp | 90° C. |
| Flush time | 2.0 min |
| Syringe | 2.5 ml HS |
| Cycle setting | |
| Cycle time | 40 min |
| Injector parameters | |
| Injection volume | 500 µl |
| Fill speed | 500 µl/s |
| Pull up delay | 1.0 s |
| Fill stroke | 0 |
| Injection speed | 500 µl/s |
| Pre Inj. Delay | 0.0 s |
| Post Inj. Delay | 0.0 s |
| Injection penetration | 40 mm |
| Multiple HS Parameters | |
| Injection per run | 1.0 |
| Delay time | 0.0 min | c) Preparation of Standard Solution

Weigh accurately respective standard in 100 ml volumetric flask containing 50 ml N,N-dimethylformamide and diluted up to the mark with N,N-dimethylformamide.

d) System Suitability Test

Carry out the system suitability test by calculating the percent Relative Standard Deviation (% RSD) of each solvent peak area and retention time for the six replicate standard solutions.

e) Specification:

% RSD of area (For each solvent): not more than 10.0%.

f) Preparation of Test Solution

Weigh accurately about 100 mg of sample in a 10 ml capacity headspace vial. Add 1 ml of N,N-dimethylformamide.

g) Procedure

Make one injection of diluent i.e. N,N-dimethylformamide.

Make six injections of standard solutions and check the system suitability parameter as mentioned in the system suitability test.

Once the system suitability parameters are met, make injection of test solution.

Example 1

Afatinib Free Base Form A

To a 50 ml single-neck round-bottom flask equipped with magnetic needle and nitrogen balloon was charged 5.0 ml (46.9 mmol) concentrated HCl, 5.0 ml water and the mixture was stirred at 30° C. After 15 min, 5.3 ml (27.1 mmol) (dimethylamino)-acetaldehyde-diethyl acetal was added over a period of 5 min at 30° C. The mixture was stirred at room temperature in an inert atmosphere overnight. The solution thus obtained was designated as reagent "A".

A 250 ml two-neck round-bottom flask equipped with magnetic needle, thermometer and nitrogen balloon was charged with 6.0 g (10.85 mmol) diethyl(4-(3-chloro-4-fluorophenylamino)-7-(S)-(tetrahydrofuran-3-yloxy)quinazoline-6-yl-carbamoyl)-methyl)-phosphonate, 0.47 g (10.85 mmol), lithium chloride anhydrous and 25 ml THF. The mixture was cooled to −8° C. in an ice-salt bath and a cold solution of potassium hydroxide (4.7 g, 82.7 mmol dissolved in 24 ml water kept at −18° C.) was added over the period of 15 min. Reagent "A" was added dropwise over the course of 30 min to the reaction mixture which was maintained at −7° C. and stirred at the same temperature for 1 h. The reaction was slowly allowed to come to 20° C. and stirred at this temperature for 45 min. 20 ml water were added and the mixture was extracted with 3×50 ml ethyl acetate. The combined extract was dried on sodium sulphate, evaporated and the resulting residue dried at 45° C. under vacuum to give a yellow solid. 200 ml water were added to the solid, the mixture was stirred for 1 h, filtered, washed with 200 ml water, dried on a rotary evaporator at 45° C. for 2 h to give 5.1 g (97.7%, 10.6 mmol) of an off-white solid.

DSC shows two endothermic peaks at 95.9° C. and 138.6° C.

IR (cm$^{-1}$): 3547.4, 2980.2, 2947.8, 2865.7, 2774, 1673.1, 1626.9, 1575.8, 1536.1, 1500.1, 1455.7, 1430.5, 1397.0, 1233.4, 1147.1, 981.9, 852.1, 778.5 and 660.9.

Example 2

Afatinib Free Base Form B 1.0 g afatinib free base was dissolved in 3 ml butylacetate and 15 ml methylcyclohexane were added slowly. The solid was filtered off and dried at 45° C. under vacuum for 2 h to yield 0.92 g of the free base.

DSC shows a broad endotherm at 98.2° C.

IR (cm$^{-1}$): 3551.1, 3117.7, 2978.0, 2947.6, 2863.7, 2821.3, 2777.1, 1735.3, 1672.0, 1630.2, 1575.5, 1534.4, 1456.4, 1432.1, 1397.4, 1234.4, 1211.4, 1146.2, 884.1, 779.8, 692.8 and 661.2.

Example 3

Afatinib Free Base Form C

A 25 ml single-neck round-bottom flask equipped with magnetic needle and nitrogen balloon was charged with 5.3 ml (51.0 mmol) concentrated hydrochloric acid and 5.7 ml water and the mixture was stirred at 30° C. After 7 min, 5.75 ml (29.4 mmol) (dimethylamino)-acetaldehyde diethyl acetal were added over a period of 5 min at 30° C. During the addition, evolution of gas was observed and the mixture became a clear colourless solution. The solution was stirred at room temperature overnight. The solution thus obtained was designated as reagent "A"

A 250 ml two-neck round-bottom flask equipped with magnetic needle, thermometer and nitrogen balloon was charged with 6.5 g (11.75 mmol) diethyl(4-(3-chloro-4-fluorophenylamino)-7-(S)-(tetrahydrofuran-3-yloxy)-quinazoline-6-yl-carbamoyl)methyl)-phosphonate, 0.51 g (11.75 mmol) anhydrous lithium chloride and 30 ml THF to obtain a clear solution. The mixture was cooled in an ice-salt bath to −6° C. and a cold potassium hydroxide solution (5.1 g, 90 mmol KOH pellets dissolved in 26 ml water and stored at −18° C. for 1 h) was added over the course of 15 min. Reagent "A" was added dropwise over the course of 1 h with the temperature maintained at −7° C. and then the mixture was stirred at the same temperature for 1 h. The ice-salt bath was replaced with a cold water bath and the mixture was allowed to warm to 20° C. gradually over a period of 30 min. Water (25 ml) was added to the reaction mixture. The mixture was extracted with 3×60 ml ethyl acetate, dried over sodium sulphate and evaporated at 40° C. under vacuum to give a solid. To this solid 200 ml water were added and the mixture was stirred for 1.5 h. The solid was filtered off, washed with 200 ml water and dried on a rotary evaporator at 40° C. under vacuum to give 6.9 g of a solid. 6.35 g of this crude product were purified by column chromatography on silica, using a gradient of chloroform to 4% MeOH in chloroform. To 388 mg of the free base thus obtained 5 ml methylcyclohexane were added and the mixture was stirred in an oil bath at 130° C. for 20 min. Another 5 ml of methylcyclohexane and 4 ml of n-butyl acetate were added. After hot filtration, the filtrate was allowed to cool to room temperature and stirred for 2.5 h. The precipitated solid was filtered off and dried on a rotary evaporator at 40° C. for 3 h to give 258 mg of an off-white product.

DSC shows two broad overlapping endothermic peaks at 95.1° C. and 100.7° C.

IR (cm$^{-1}$): 3545.2, 3340.5, 2980.1, 2946.7, 2775.2, 1736.1, 1672.0, 1632.2, 1575.1, 1536.6, 1500.1, 1458.1, 1400.4, 1340.7, 1243.1, 1212.0, 1149.4, 1084.2, 970.1, 883.1, 852.3, 780.6, 692.6, 661.3 and 540.2.

Example 4

Afatinib Free Base Form D

A 5 ml single-neck flask equipped with magnetic needle and nitrogen balloon was charged with 0.7 ml (7.6 mmol) concentrated hydrochloric acid and 0.7 ml water and the mixture was stirred at 30° C. After 10 min, 0.7 ml (3.4 mmol) (dimethylamino) acetaldehyde diethyl acetal was added over a period of 20 min at 30° C. During the addition, evolution of gas was observed and a colourless solution was obtained. The reaction mixture was stirred at 35° C. for 3.5 h. The solution thus obtained was designated as reagent "A".

A 50 ml two-neck round-bottom flask equipped with magnetic needle and nitrogen balloon was charged with 0.8 g (1.4 mmol) diethyl(4-(3-chloro-4-fluorophenylamino)-7(S)-(tetrahydrofuran-3-yloxy)-quinazoline-6-yl-carbamoyl)methyl) phosphonate, 0.06 g (1.4 mmol) anhydrous lithium chloride and 4 ml THF. The reaction mixture was stirred at room temperature for 5 min and subsequently cooled to −5° C. in an ice-salt bath for 15 min. A cold potassium hydroxide solution (0.63 g KOH pellets dissolved in 3.2 ml water and stored at −18° C. for 1 h) was added. Reagent "A" was added to the reaction mixture at −7° C. over the course of 3 min and the resulting mixture was stirred at −5° C. for 1 h. The ice-salt bath was replaced with a cold water bath at 17° C. The reaction mixture was cooled to 2° C. and 29 ml water was added over the course of 30 min. This solid was filtered off, washed with 20 ml water and dried on a Buchner funnel. Subsequently, the solid was dried at room temperature under vacuum for 16 h to give 0.62 g (90%, 1.3 mmol) of an off-white solid. To 0.45 g of the free base thus obtained 3 ml n-butyl acetate were added and the mixture was stirred at 140° C. for 20 min to obtain a clear solution and then allowed to cool to room temperature for 30 min. A 1:3 mixture of n-butyl acetate and methylcyclohexane (4 ml) was added and the mixture was stirred for 15 min. The solid formed and was filtered off, washed with 8 ml methylcyclohexane and dried on a rotary evaporator at 50° C. under vacuum for 3.3 h to give 415 mg of an off-white solid.

DSC shows an endotherm at 98.2° C.

IR (cm$^{-1}$): 3551.1, 3117.7, 2978.0, 2947.6, 2863.7, 2821.3, 2777.1, 1735.3, 1672.0, 1630.2, 1575.5, 1534.4, 1456.4, 1432.1, 1397.4, 1234.4, 1211.4, 1146.2, 884.1, 779.8, 692.8 and 661.2.

Example 5

Afatinib Dimaleate Form B

THF (0.5 ml) was added to 200 mg (0.41 mmol) afatinib free base and the mixture was stirred at room temperature to obtain a light yellow coloured solution. A solution of 100 mg (0.8 mmol) maleic acid in 0.5 ml THF was added over the course of 2 min. Another 4 ml THF were added and the mixture was stirred for 1 h. The solids were filtered off, rinsed with 2 ml THF and dried on a rotary evaporator at 48° C./3 mbar for 6 h to give 0.245 g (83% yield) of a white solid.

DSC shows an exotherm at 125.9° C. followed by a minor endotherm at 156.8 and a major endotherm at 173.9° C.

XRPD confirms crystalline nature.

IR (cm$^{-1}$): 3321.2, 3034.0, 1687.6, 1643.6, 1498, 1456.6, 1353.4, 1268.4, 1067.5, 869.0, 780, 654.7 and 576.4.

Residual solvent: THF=3390 ppm.

Example 6

Afatinib Dibenzenesulphonate

Ethanol (2 ml) was added to 200 mg (0.41 mmol) afatinib free base and the solution was stirred at 70° C. for 15 min. A solution of 130 mg (0.8 mmol) benzenesulphonic acid in 1 ml ethanol was added at 70° C. over the course of 2 min and the solution was stirred for another 10 min. Heating was switched off and the solution was allowed to cool to room temperature over the course of 2.5 h. Diethyl ether (2.5 ml) was added and the solution was concentrated to dryness. 3 ml ethyl acetate were added and the solid was filtered off. Drying at 50° C. at 5 mbar for 5 h yielded 0.21 g (63.6%, 0.3 mmol) of a light yellow solid.

IR (cm$^{-1}$): 3050.7, 1691.1, 1637.3, 1577, 1523.9, 1498.3, 1448.2, 1219.4, 1124.0, 1068.8, 1034.4, 1016.7, 997, 728.2, 694.8, 612.3 and 565.7.

Residual solvent: ethyl acetate=0.74%.

Example 7

Afatinib Fumarate Form A

Ethanol (2 ml) was added to 200 mg (0.4 mmol) afatinib free base and the mixture was stirred at 70° C. to obtain a light yellow coloured solution. A solution of 100 mg (0.8 mmol) fumaric acid in 2.5 ml ethanol was added at 70° C. over the course of 2 min and the solution was stirred for 10 min. Heating was stopped and the mixture was allowed to cool to room temperature. 2.5 ml diethyl ether was added to obtain a turbid solution. The reaction mixture was stirred for 1 h, which resulted in a solid. The solid was filtered off, dried at 48° C. at 5 mbar for 5 h to obtain 0.2 g (67.7%, 0.3 mmol) of an off-white solid.

DSC shows two broad endothermic peaks at 67.3° C., 126.8° C. and a broad exothermic peak at 169.0° C.

IR (cm$^{-1}$): 2982.5, 1679.7, 1530.5, 1499.8, 1428.4, 1214.1, 1144.5, 980.0, 672.8 and 540.2

Residual solvent: ethanol=3.26%, diethyl ether=547 ppm.
$^1$H NMR indicates presence of a monofumarate.

Example 8

Afatinib Disulphate Form A

Ethyl acetate (2 ml) was added to 200 mg (0.41 mmol) afatinib free base and the mixture was stirred at room temperature to obtain a light yellow coloured solution. A solution of 0.09 ml (1.6 mmol) sulphuric acid in 1 ml ethyl acetate was added at room temperature over the course of 2 min. Precipitation was observed immediately upon addition of the acid. A sticky solid was observed. 3 ml ethyl acetate was added and stirring continued for 2.5 h. The solid was filtered off and dried on a rotary evaporator at 50° C./3 mbar for 3 h to give 263 mg (94%) of a light yellow solid.
DSC shows a sharp endothermic peak at 127.2° C.
IR (cm$^{-1}$): 3029.6, 1636.3, 1572.7, 1497.8, 1231.9, 1055.3, 882.4 and 581.
Residual solvent: ethanol=1.13%, ethyl acetate=1.27%.

Example 9

Afatinib Disulphate Form B

To 200 mg (0.4 mmol) afatinib free base, 1.5 ml ethanol-water (99:1) was added and the light yellow solution was stirred at 50° C. for 15 min. A solution of 85 mg (0.8 mmol) H$_2$SO$_4$ in 0.5 ml ethanol-water (99:1) was added over the course of 2 min. Upon addition of the acid, a solid started to precipitate out. Another 0.5 ml ethanol-water (99:1) was added and the mixture was stirred at 85° C. to obtain a clear solution after 5 min. Heating was switched off after 15 min and the mixture was allowed to cool to room temperature. After 1 h, the reaction mixture was diluted with 1 ml ethanol-water (99:1), the solid was filtered off, dried on a rotary evaporator at 5 mbar for 5.5 h to give 200 mg (72%) of an off-white solid.
IR (cm$^{-1}$): 3295.9, 1695.5, 1637.8, 1573.2, 1497.1, 1449.6, 1268.7, 1216.9, 1197.8, 1050.8, 874.1, 776.4 and 583.1.
Residual solvent: ethanol—not detected.

Example 10

Afatinib Dihydrochloride Form A

IPA (2 ml) was added to 200 mg (0.41 mmol) afatinib free base and the light yellow solution was stirred for 5 min at room temperature. HCl in IPA (1.5 ml) was added over the course of 4 min. Precipitation was observed and the mixture was diluted with 1 ml IPA and stirred at room temperature for 1.25 h. The reaction mixture was further diluted with 3 ml IPA, the solid was filtered off and dried on a rotary evaporator at 50° C./3 mbar for 7 h to give 184 mg (80%) of a yellow solid.
IR (cm$^{-1}$): 2961.6, 1680.8, 1633.5, 1572.7, 1523.4, 1499, 1477.8, 1266.0, 1067.2, 887.4 and 778.3.
Residual solvent: IPA=1.87%; ethyl acetate=729 ppm Example 11

Afatinib Dioxalate Form A

Ethanol (3 ml) was added to 200 mg (0.41 mmol) afatinib free base and the mixture was heated to 40° C. to get a light yellow solution. A solution of 70 mg (0.8 mmol) oxalic acid in 1 ml ethanol was added at 40° C. and the reaction mixture was heated under reflux conditions for 50 min. The reaction temperature was allowed to cool to ambient temperature and 3 ml ethanol was added. The solid was filtered off and dried at 60° C./3 mbar for 5.5 h to give 215 mg (78%) of an off-white solid.
DSC shows a sharp endotherm at 185.4° C. followed by an exotherm at 190.7° C.
IR (cm$^{-1}$): 3041.5, 2867, 1776.2, 1702, 1640.3, 1522.9, 1500.1, 1454, 1402.6, 1329.1.

Example 12

Afatinib Dimesylate Form A

Ethyl acetate (2 ml) was added to 200 mg (0.41 mmol) afatinib free base and the light yellow solution was stirred at room temperature. A solution of 80 mg (0.8 mmol) methanesulphonic acid in 1 ml ethyl acetate was added at room temperature over the course of 2 min. Precipitation was observed and another 4 ml ethyl acetate was added. After stirring at ambient temperature for 40 min the solid was filtered off, washed with 3 ml ethyl acetate and dried at 48° C./3 mbar for 4.5 h to give 257 mg (92%) of a light yellow solid.
Melting point=180-188° C.
IR (cm$^{-1}$): 3018.1, 1692.8, 1638.5, 1498.5, 1455, 1367.2, 1271.4, 1207.8, 1194.4, 1058.9, 783.9 and 554.7.
Residual solvent: ethyl acetate=46.3 ppm.

Example 13

Afatinib Dimesylate Form B 1.5 ml ethanol-water (99:1) was added to 200 mg (0.41 mmol) afatinib free base and the light yellow solution was stirred at 70° C. for 5 min. A solution of 80 mg (0.8 mmol) methanesulphonic acid in 0.5 ml ethanol-water (99:1) was added over the course of 2 min. Another 0.5 ml ethanol-water (99:1) was added to the reaction mixture and stirring continued for 15 min. The heating was switched off and the mixture was allowed to cool to room temperature and stirred for 15 h to obtain a thick solid. The reaction mixture was diluted with 4 ml ethanol-water (99:1), the solid was filtered off and dried on a rotary evaporator at 3 mbar for 4.5 h to give 190 mg (68%) of an off white solid.
DSC shows a broad endothermic peak at 106.1° C., followed by an endothermic peak at 182.8 and 191.5° C.
IR (cm$^{-1}$): 3018.1, 1692.8, 1638.5, 1498.5, 1455, 1367.2, 1271.4, 1207.8, 1194.4, 1058.9, 783.9 and 554.7. IR is different as compared to 043/190.
Residual solvent: Ethanol=779 ppm.

Example 14

Afatinib Diphosphate Amorphous

Ethyl acetate (2 ml) was added to 200 mg (0.41 mmol) afatinib free base and the light yellow solution was stirred at room temperature. A solution of 80 mg (0.8 mmol) phosphoric acid in 1 ml ethyl acetate was added over the course of 2 min at room temperature. Precipitation was observed and more ethyl acetate (5 ml) was added and stirring continued at room temperature for 50 min. The solid was filtered off, washed with 3 ml ethyl acetate and dried at 48° C./3 mbar for 5 h to give 289 mg (93%) of a light yellow solid.

IR (cm$^{-1}$): 2879.6, 1741.1, 1684.6, 1639.4, 1574.8, 1498.0, 1455.3, 1265.1, 965.6 and 778.2.

Residual solvent: ethyl acetate=4.91%.

Example 15

Afatinib Diphosphate Form A

Ethanol-water (99:1) 1.5 ml was added to 200 mg (0.41 mmol) afatinib free base and the light yellow solution was stirred at 80° C. for 10 min. A solution of 80 mg (0.8 mmol) phosphoric acid in 0.5 ml ethanol-water (99:1) was added over the course of 2 min at 80° C. Another 1.5 ml ethanol-water (99:1) was added and stirring continued for 25 min. The reaction mixture was allowed to cool to room temperature and then diluted with 3 ml ethanol-water (99:1). After 1.5 h the solid was filtered off and dried on a rotary evaporator at 3 mbar/52° C. for 5 h to give 250 mg (85%) of an off-white solid.

DSC shows a minor endothermic peak at 109.3° C., a small exothermic peak at 145.3° C., followed by an endothermic peak at 166.1° C. and an exothermic peak at 178.3° C.

IR (cm$^{-1}$): 3018.1, 1692.8, 1638.5, 1498.5, 1455, 1367.2, 1271.4, 1207.8, 1194.4, 1058.9, 783.9 and 554.7.

Residual solvent: ethanol >5000 ppm.

Example 16

Afatinib Di-L-Malate Amorphous

Ethyl acetate (2 ml) was added to 200 mg (0.41 mmol) afatinib free base and the light yellow solution was stirred at room temperature. A solution of 110 mg (0.8 mmol) L-malic acid in 3 ml ethyl acetate was added over the course of 2 min at room temperature. Precipitation was observed and ethyl acetate (5 ml) was added. The mixture was stirred at room temperature for 1 h. The solid was filtered off, washed with 2 ml ethyl acetate and dried at 48° C./3 mbar for 6 h to give 251 mg (80.7%) of a light yellow solid.

IR (cm$^{-1}$): 2983.9, 1719.3, 1535.8, 1498.4, 1263.8, 879.4 and 778.2.

Residual solvent: ethyl acetate=5.37%.

Example 17

Afatinib Citrate Amorphous

Ethanol (2 ml) was added to 100 mg (0.205 mmol) afatinib free base and the light yellow solution was stirred at room temperature. A solution of 39.4 mg (0.205 mmol) citric acid in 0.5 ml ethanol was added over the course of 2 min. Another 0.5 ml ethanol was added. Precipitation was observed and the mixture was stirred for 15 min. The solid was filtered, washed with 0.5 ml ethanol and dried on rotary evaporator at 50° C. for 2 h to give 80 mg (57%) of a light yellow solid.

DSC shows no distinct peaks.

IR (cm$^{-1}$): 2972.8, 1717.1, 1625.3, 1576.2, 1535.5, 1498.6, 1213.1, 879.3 and 778.9.

Example 18

Afatinib Disuccinate Form A

Ethyl acetate (2 ml) was added to 200 mg (0.41 mmol) afatinib free base and the light yellow solution was stirred at room temperature. A solution of 100 mg (0.8 mmol) succinic acid in 2 ml ethanol was added over the course of 2 min. The mixture was stirred for 6.5 h and concentrated to ~1 ml. To this residue, 3 ml ethyl acetate was added and the resulting mixture was stirred at room temperature for 1.5 h. The solid was filtered off, washed with 2 ml ethyl acetate and dried at 50° C./4 mbar for 5 h to give 225 mg (75.7%) of an off-white solid.

DSC shows two endothermic peaks at 97.1° C. and 103.7° C. and a broad exothermic peak at 157.3° C.

IR (cm$^{-1}$): 3002.7, 1934.7, 1738.7, 1709.0, 1626, 1581.3, 1532.6, 1494.6, 1428.2, 1210.3, 979.1, 797.8, 654.0 and 532.

Residual solvent: Ethyl acetate=4.22%, ethanol=0.43%.

Example 19

Afatinib Di-L-Aspartate Form A

Water (4 ml) was added to 110 mg (0.8 mmol) L-aspartic acid and the mixture was stirred at 110° C. A solution of 200 mg (0.41 mmol) afatinib free base in 1 ml THF was added. The mixture was stirred for 30 min. The heating was switched off and the mixture was allowed to cool to room temperature. Another 2 ml THF was added and stirring continued at room temperature. After one week the mixture was concentrated on a rotary evaporator to give 0.3 g (97% yield) of a light yellow solid.

DSC shows endothermic peaks at 134.8° C., 158.8° C., 167.5° C., 222.1° C. and 255.3° C.

IR (cm$^{-1}$): 3411.4, 2986.7, 1688, 1625.5, 1534.4, 1498.2, 1425.9, 1208.6, 1054, 899.9, 659.3 and 552.1.

Residual solvent: THF=not detected.

Example 20

Afatinib Difumarate

A mixture of ethanol and water (95:5) (1 ml) was added to 200 mg (0.41 mmol) afatinib free base and the mixture was stirred at room temperature to obtain a clear light yellow coloured solution. A solution of 100 mg (0.8 mmol) fumaric acid in 2.5 ml of a mixture of ethanol and water (95:5) was added over the course of 2 min. After 3 min a solid crystallized out and stirring was continued at room temperature for 1 h. The solid was filtered off and washed with a mixture of ethanol and water (95:5) and dried at 62° C. at 3 mbar for 4.5 h to obtain 220 mg (74%, 0.3 mmol) of an off-white solid.

DSC shows three broad endotherms at 81.5, ° C., 117.4° C. and 182.1° C.

IR (cm$^{-1}$): 3560.1, 3412.5, 3287.9 1707.1 1654.9, 1497.8, 1463.9, 1212.9, 1171.7, 981.1.

Further aspects and features of the present invention are set out in the following numbered clauses:

1. Active pharmaceutical ingredient selected from afatinib free base in polymorphic form A, afatinib free base in polymorphic form B, afatinib free base in polymorphic form C, afatinib free base in polymorphic form D, and salts of the afatinib free base with one or more acid compounds of the Formula $H_mX$, wherein H is a dissociable hydrogen atom, X is a pharmaceutically acceptable residue and m is a natural number. Provided that X is not tartrate and provided that if X is maleate or fumarate, then the afatinib salts are present in afatinib dimaleate form B or afatinib fumarate form A.

2. A salt of afatinib according to clause 1, wherein the acid compound is an organic acid with between 1 and 13 carbon atoms.

3. A salt of afatinib according any of the preceding clauses, wherein the acid compound has a melting point of between 5° C. and 275° C.

4. A salt of afatinib according to any of the preceding clauses, wherein the acid compound is selected from maleic acid, fumaric acid, benzenesulphonic acid, sulphuric acid, oxalic acid, hydrochloric acid, methanesulphonic acid, phosphoric acid, L-malic acid, citric acid, succinic acid and/or L-aspartic acid.

5. An active pharmaceutical ingredient according to any of the preceding clauses, in the form of a hydrate and/or a solvate, preferably having a water content of 0.1 to 8 wt.-% and/or having a residual solvent content of 0.01 to 6 wt.-%, based on the total weight of the active pharmaceutical ingredient.

6. A process for the manufacture of an active pharmaceutical ingredient according to any of the preceding clauses, wherein
(i) the free base compound and/or the corresponding acid compound is dissolved in an organic solvent,
(ii) the solution or solutions of (i) are mixed with each other,
(iii) optionally, the solution of (ii) is stirred,
(iv) the solution is kept without stirring under conditions acceptable for salt crystallization,
(v) the salt precipitate is separated and dried.

7. A pharmaceutical composition, comprising an active pharmaceutical ingredient according to any of clauses 1 to 5 and at least one pharmaceutically acceptable excipient and/or additive.

8. A pharmaceutical composition according to clause 10, wherein the pharmaceutical composition comprises from 5 to 80 mg of the active pharmaceutical ingredient according to any of clauses 1 to 5.

9. A pharmaceutical composition according to clauses 7 or 8, comprising at least one further active ingredient selected from paclitaxel, cis-platin, pemetrexed, vinorelbine, simvastatin, letrozole, intedanib, bevacizumab, temozolomide, rapamycin, herceptin and cetuximab as well as pharmaceutical acceptable salts thereof.

10. A pharmaceutical composition according to clause 9, wherein the second active pharmaceutical ingredient is present in an amount of 1 to 200 mg.

11. A pharmaceutical composition for treating tumours or respiratory or gastrointestinal diseases, wherein the composition is applied once daily, once weekly, twice weekly or thrice weekly.

What is claimed is:

1. Crystalline difumarate salt of afatinib.

2. The difumarate salt of afatinib according to claim 1, characterised by data selected from the group consisting of:
an XRPD pattern having peaks at 4.6±0.2, 24.8±0.2 and 26.1±0.2 ° 2-Theta,
an XRPD pattern substantially as depicted in FIG. 20;
and a combination thereof.

3. Crystalline dioxalate salt of afatinib.

4. The dioxalate salt of afatinib according to claim 3, characterised by data selected from the group consisting of:
an XRPD pattern having peaks at 5.6±0.2, 23.5±0.2 and 25.3±0.2 ° 2-Theta,
an XRPD pattern substantially as depicted in FIG. 11;
and a combination thereof.

5. Crystalline dimesylate salt of afatinib.

6. The dimesylate salt of afatinib: according to claim 5, characterised by data selected from the group consisting of:
an XRPD pattern having peaks at 19.5±0.2, 25.3±0.2 and 25.7±0.2 ° 2-Theta,
an XRPD pattern substantially as depicted in FIG. 12;
and a combination thereof.

7. The A dimesylate salt of afatinib characterised by data selected from the group consisting of:
an XRPD pattern having peaks at 15.0±0.2, 21.0±0.2 and 26.7±0.2 ° 2-Theta,
an XRPD pattern substantially as depicted in FIG. 13;
and a combination thereof.

8. A solid pharmaceutical composition comprising one or more of a crystalline form thereof selected from the group consisting of
the afatinib salt according to claim 1; the afatinib salt according to claim 2,
the afatinib salt according to claim 3; the afatinib salt according to claim 4,
the afatinib salt according to claim 5; the afatinib salt according to claim 6, and
the afatinib salt according to claim 7
and at least one solid pharmaceutically acceptable excipient.

9. A method of treating a solid tumor selected from the group consisting of NSCLC, breast, head, and neck cancer in a person, comprising administering a therapeutically effective amount of at least one afatinib salt or the crystalline forms thereof selected from the group consisting of
the afatinib salt according to claim 1; the afatinib salt according to claim 2,
the afatinib salt according to claim 3; the afatinib salt according to claim 4,
the afatinib salt according to claim 5; the afatinib salt according to claim 6, and
the afatinib salt according to claim 7
to a person suffering from cancer.

* * * * *